United States Patent [19]

Schick et al.

[11] Patent Number: 5,264,348
[45] Date of Patent: Nov. 23, 1993

[54] ASCORBATE INTERFERENCE-RESISTANT COMPOSITION, DEVICE AND METHOD OF ASSAYING FOR PREDETERMINED ANALYTE

[75] Inventors: Lloyd A. Schick, Bristol; Meitak T. Yip, Elkhart, both of Ind.

[73] Assignee: Miles Inc., Elkhart, Ind.

[21] Appl. No.: 699,317

[22] Filed: May 13, 1991

[51] Int. Cl.$^5$ .......................... C12Q 1/28; G01N 33/20
[52] U.S. Cl. ........................................ 435/28; 435/4; 435/10; 435/11; 435/14; 435/25; 436/66; 436/73; 436/74; 436/800; 436/904
[58] Field of Search ........................ 435/2, 8, 4, 10, 11, 435/14, 25; 436/66, 73, 74, 800, 904

[56] References Cited

U.S. PATENT DOCUMENTS 5,079,140  1/1992  Albarella et al. .................... 435/4

OTHER PUBLICATIONS

Birk, *Inorg. Chem.*, vol. 12, pp. 2468-2472, 1973.
Birk et al., *Inorg. Chem.*, vol. 17, pp. 1186-1191, 1978.
Kozub, *Ph.D. Dissertation, Xerox University Microfilms*, Ann Arbor, 1975.

*Primary Examiner*—Michael G. Wityshyn
*Assistant Examiner*—Abdel A. Mohamed
*Attorney, Agent, or Firm*—Roger N. Coe

[57] ABSTRACT

A new and improved test device and method of determining the presence or concentration of a predetermined analyte, such as glucose, cholesterol or occult blood, in a test sample are disclosed. The test device includes a test pad comprising a suitable carrier matrix incorporating an indicator reagent composition capable of interacting with the predetermined analyte to produce a detectable or measurable response. In addition, the new and improved indicator reagent composition, comprising an indicator dye, such as a redox indicator, like a benzidine indicator; a redox mediator, such as an oxidase enzyme capable of interacting with the predetermined analyte and a peroxidase enzyme; a metal ion complex; and a cooxidant selected from the group consisting of bromate ion, chlorate ion, perchlorate ion, chromate ion, an organic oxidant like a peroxide, a hydroperoxide or a N-halo compound, and combinations thereof, is incorporated into the carrier matrix to provide a more accurate, ascorbate interference-resistant assay of a test sample for the predetermined analyte.

60 Claims, 3 Drawing Sheets

ASCORBATE INTERFERENCE-RESISTANT COMPOSITION, DEVICE AND METHOD OF ASSAYING FOR PREDETERMINED ANALYTE

FIELD OF THE INVENTION

The present invention relates to a composition, device and method of determining the presence or concentration of a predetermined analyte in a test sample. More particularly, the present invention relates to a new and improved method of assaying a liquid test sample, like a biological sample, such as urine, blood plasma or blood serum, for a predetermined analyte, like an analyte capable of interacting with an oxidase enzyme, such as glucose or cholesterol, or like a peroxidatively active substance, such as occult blood, by utilizing an indicator reagent composition that effectively resists ascorbate interference. The indicator reagent composition undergoes a detectable or a measurable response upon contact with a test sample containing the predetermined analyte. The indicator reagent composition of the present invention provides a more accurate and sensitive assay for the predetermined analyte by essentially eliminating the interfering affects of ascorbate present in the test sample. Accordingly, the improved sensitivity achieved by the indicator reagent composition of the present invention provides an improved method of assaying a test sample for a low concentration of a predetermined analyte, such as assaying urine for occult blood or glucose, or assaying blood serum or blood plasma for glucose.

BACKGROUND OF THE INVENTION AND PRIOR ART

As used here, and hereinafter, the expression "predetermined analyte" is defined as a compound either (a) that is capable of interacting with an oxidase enzyme to generate hydrogen peroxide or (b) that exhibits peroxidative activity. Similarly, as used here, and hereinafter, the expression "redox mediator" is defined as a compound, or compounds, capable of interacting with a predetermined analyte to generate molecular oxygen. The molecular oxygen, in turn, oxidizes an oxidizable dye to provide a detectable color change. The "redox mediator" can be a combination of an oxidase enzyme and peroxidase enzyme, or can be a hydroperoxide, depending upon the particular predetermined analyte of interest. Therefore, assays for a predetermined analyte, like an analyte capable of interacting with a suitable oxidase enzyme and peroxidase, such as glucose, or like a peroxidatively active substance, such as occult blood, i.e., hemoglobin, are based upon a chromogenic interaction, wherein the degree and intensity of a color transition of an oxidizable indicator dye are correlated to the concentration of the predetermined analyte in a test sample. Assays for a predetermined analyte are particularly useful in detecting and measuring low concentrations of analyte in body fluid samples such as blood, urine, feces or gastrointestinal contents.

For example, glucose is the sugar most commonly found in urine. The presence of detectable amounts of glucose in urine is known as glycosuria. Glycosuria can be a benign or a pathological condition, and the physician must distinguish between the two types.

Glycosuria can occur when blood glucose levels are normal because reabsorption of glucose in the kidneys is below normal, thus permitting some glucose to spill into the urine. This is a benign condition, as is the occurrence of glycosuria after eating a heavy meal or in conjunction with emotional stress. However, diabetes mellitus is a pathological state and is the chief cause of glycosuria. Indications of diabetes mellitus include a marked elevation of blood glucose and an increase in urine volume. The urine glucose content of a diabetic individual can be as high as 10%, with a content of 2% to 5% commonly being found.

Various assays are available to test urine for glucose. The most commonly used assay is an enzymatic test based on an interaction between glucose oxidase and glucose. The enzymatic glucose oxidase test for glucose, as applied to urine, is specific for glucose. Other sugars, such as lactose, fructose, galactose and pentose, are not substrates for the glucose oxidase enzyme, and, therefore, are not detected or measured.

In a standard assay of a test sample for glucose, glucose oxidase, in the presence of oxygen, first converts the glucose in the test sample to gluconic acid and hydrogen peroxide. Then, the peroxidase enzyme, also present in the assay, catalyzes an interaction between the hydrogen peroxide and an oxidizable dye compound, like o-tolidine. The dye compound, usually essentially colorless in its reduced state, undergoes a color transition upon oxidation, such as to a blue color for o-tolidine, by the peroxidase-catalyzed interaction with hydrogen peroxide. The degree and intensity of the color transition are directly proportional to the amount of hydrogen peroxide generated by the glucose conversion. Then, the amount of hydrogen peroxide generated by the glucose conversion is correlated to the original concentration of glucose in the urine sample. In practice, a test strip is dipped into the urine sample, and the resulting color transition of the test strip is compared to a color chart ranging from colorless, indicating less than 0.1% concentration of glucose, to blue, indicating a 2.0% or greater concentration in the urine.

Peroxidase is an enzyme that catalyzes the oxidation of various compounds, such as phenols and amines, by peroxides. In addition, particular compounds have been termed pseudoperoxidases because these compounds behave in a manner similar to the peroxidase enzyme. Accordingly, pseudoperoxidases liberate oxygen from hydroperoxides, and transfer the oxygen to certain acceptor compounds. Therefore, in general, the pseudoperoxidases are enzyme-like in that they catalyze, or otherwise participate in, interactions between peroxides and oxidizable compounds, like oxidizable dye compounds. The pseudoperoxidases also are termed peroxidatively active substances, and include hemoglobin and its derivatives.

Therefore, a peroxidatively active substance, like hemoglobin, a hemoglobin derivative, an erythrocyte, myoglobin or a combination thereof, catalyzes an interaction between a hydroperoxide and an oxidizable dye. In such interactions, the peroxidatively active substance imitates the peroxidase enzyme, and catalyzes or otherwise participates in an interaction between the oxidizable dye and the hydroperoxide. The oxygen liberated from a hydroperoxide by a peroxidatively active substance is transferred to an oxidizable dye. The resulting interaction provides a detectable response, such as a color transition, wherein the intensity and degree of the response are indicative of the presence or the concentration of the peroxidatively active substance.

For example, a low concentration of blood in the urine is termed "occult blood." Occult blood is detected by assaying for the peroxidatively active compound hemoglobin. Although occult blood in urine, feces or vomit usually is not visible to the naked eye, the detection of occult blood is important in the diagnosis of hemorrhages in the stomach, intestines and urinary tract. The hemorrhages are caused, for example, by tumors, ulcers or inflammations of the organ in question. Presently, most methods of determining the presence of occult blood in a test sample are based upon the pseudoperoxidase activity of hemoglobin or myoglobin.

The presence of blood in urine also is an indication of damage to the kidney or urinary tract. Normally, detectable amounts of occult blood are not present in urine, even with very sensitive chemical methods. The presence of blood in urine or feces is a symptom of a variety of abnormal conditions, including cancer. The presence of blood in urine, as indicated by a positive test for occult blood, often indicates bleeding in the urinary tract. Free hemoglobin is present in the urine because of renal disorders, infectious diseases, neoplasms, or traumas affecting part of the urinary tract. Free hemoglobin in the urine also can indicate a transfusion reaction, hemolytic anemia, or paroxysmal hemoglobinuria, or can appear from various poisonings or following severe burns.

Therefore, accurate and sensitive assays of blood, urine and other test samples for various predetermined analytes must be available for both laboratory and home use. The assays should provide an accurate detection and measurement of the predetermined analyte such that a correct diagnosis can be made and correct medical treatment implemented, monitored and maintained. In addition, it would be advantageous if the assay method could be utilized in a dip-and-read format for the easy and economical, qualitative or quantitative determination of a predetermined analyte in blood, urine or other test samples.

Furthermore, any method of assaying for a particular predetermined analyte in blood, urine or other test samples must yield accurate, trustworthy and reproducible results by utilizing an indicator reagent composition that undergoes a color transition as a result of an interaction with the predetermined analyte, and not as a result of a competing chemical or physical interaction, such as a preferential interaction with a test sample component, like ascorbate, other than the predetermined analyte. Moreover, it would be advantageous if the assay method for the predetermined analyte is suitable for use in dry phase reagent strips for the rapid, economical and accurate determination of the predetermined analyte in blood, urine or other test samples. Additionally, the method and composition utilized in the assay for the predetermined analyte should not adversely affect or interfere with the other test reagent pads that are present on multideterminant reagent strips.

In order to determine if a body fluid of an individual includes a clinically-significant amount of a predetermined analyte, and in order to monitor the course of medical treatment to determine the effectiveness of the treatment, simple, accurate and inexpensive detection assays for predetermined analytes, like glucose and occult blood, have been developed. Furthermore, of the several different assay methods developed for the detection or measurement of a predetermined analyte in a test sample, the methods based on dip-and-read dry phase test strips have proven especially useful because dry phase test strip methods are readily automated and provide reproducible and accurate results.

Some test strips used in assays for a predetermined analyte have a single test area consisting of a small square pad of a suitable carrier matrix impregnated with an indicator reagent composition capable of interacting with the predetermined analyte and undergoing a detectable or measurable change, such as a color transition. Other test strips are multideterminant reagent strips that include one test area for the assay of a particular predetermined analyte as described above, and further include several additional test areas on the same strip to permit the simultaneous assay of other clinically-important constituents present in the test sample. For both types of colorimetric test strips, the assay for a predetermined analyte in the test sample, such as blood or urine, is performed simply by dipping the colorimetric test strip into the test sample, then comparing the resulting color of the test area of the test strip to a standardized color chart provided on the colorimetric test strip bottle. For example, glucose and occult blood tests usually are included on multideterminant reagent strips to screen urine samples during routine physical examinations because it is important to detect excess amounts of these urinary constituents early.

The test strip method is the simplest and most direct assay for the presence of a predetermined analyte. In an assay for glucose, the test area incorporates an oxidizable indicator dye, like 3,3',5,5'-tetramethylbenzidine; glucose oxidase; and peroxidase. In an assay for occult blood, the test area incorporates an oxidizable indicator dye and a hydroperoxide. In either assay, the test area undergoes a color transition in response to an interaction between the predetermined analyte present in the test sample and the glucose oxidase-peroxidase couple, or the hydroperoxide, to oxidize the tetramethylbenzidine. In accordance with the above-described method, an individual can readily determine, visually, the concentration of the predetermined analyte in a urine sample by comparing the color of the test strip to a color chart shortly after the test strip is dipped into the test sample.

However, ascorbic acid or ascorbate ion, when present in a test sample, seriously interferes in the above-described oxidation-reduction assay method for a predetermined analyte. The most common form of ascorbic acid typically is referred to as Vitamin C. This vitamin is a vital nutrient and is found in many naturally-occurring foods, such as fruits and vegetables. Vitamin C also can be synthesized and is therefore available as a food additive or in tablet form. The health benefits of Vitamin C have been known for some time, as a result, Vitamin C is a relatively popular nutrient. Therefore, Vitamin C is a popular food additive and a popular component of vitamin pills and the like.

However, the human body generally absorbs Vitamin C only to the extent necessary to meet short term needs. The vitamin usually is not stored within the body, and excess Vitamin C typically is disposed of through the urinary system. As a result, Vitamin C commonly is present in urine samples undergoing clinical assays.

Ascorbic acid is a reducing agent that can interfere in clinical assays by reducing the oxidized, colored form of an indicator dye to the reduced, colorless form of the dye. However, ascorbic acid can be oxidized. Therefore, if the ascorbic acid is oxidized before it can interact with the oxidized indicator dye, the ascorbic acid cannot act as a reducing agent and accordingly cannot interfere with the assay for a predetermined analyte.

Either in the literature or during in-house screening studies, it has been found that including certain metal ion complexes in the indicator reagent composition helps eliminate the ascorbate interference problem. However, a metal ion complex also can oxidize the dye chemically or can demonstrate peroxidase activity, and behave similarly to peroxidase enzyme or to a pseudoperoxidase, to catalyze the color-forming reaction between hydrogen peroxide or a hydroperoxide and an oxidizable dye. Accordingly, although a metal ion complex eliminates ascorbate interference, the metal ion complex may produce false positive assays.

Investigators have found that particular ferric ion complexes substantially reduce the false positive assay results attributed to some metal ion complexes used to eliminate ascorbate interference. Ascorbic acid interferences are eliminated because ascorbic acid is oxidized by ferric ion or by ferric ion complexes. Representative publications illustrating the ferric ion oxidation of ascorbic acid include:

E. Pelizetti et al., "Kinetics and Mechanism of the Oxidation of Ascorbic Acid by Tris(1,10-phenanthroline)iron(III) and Its Derivatives in Aqueous Acidic Perchlorate Media", *Inorg. Chem.*, 15, pp. 2898–2900 (1976), wherein ascorbic acid was reacted with tris(1,10-phenanthroline)iron(III) in aqueous perchlorate over a pH range of one to 3.5, with the rate of oxidation decreasing with increasing pH;

L. S. Vann, "A Rapid Micro Method for Determination of Ascorbic Acid in Urine by Ferric Reduction", *Clin. Chem.*, 11, pp. 979–985 (1965);

M. M. T. Khan et al., "The Kinetics of the Reaction of Iron (III) Chelates of Aminopolycarboxylic Acids with Ascorbic Acid", *J. Am. Chem. Soc.*, 90, pp. 3386–3389 (1968) and M. M. T. Khan et al., *J. Am. Chem. Soc.*, 89, p. 7104 (1967), wherein the kinetics of ascorbic acid oxidation in the presence of ferric and cupric chelates in the pH range of 1.8 to 3.45 is discussed;

G. S. Laurence et al., "The Detection of a Complex Intermediate in the Oxidation of Ascorbic Acid by Ferric Ion", *J. Chem. Soc. Dalton Trans.*, pp. 1667–1670 (1972);

W. C. Butts et al., "Centrifugal Analyzer Determination of Ascorbate in Serum and Urine with $Fe^{3+}$/Ferrozine", *Clin. Chem.*, 21, pp. 1493–1497 (1975);

L. Pekkarinen, "The Mechanism of the Autoxidation of Ascorbic Acid Catalyzed by Iron Salts in Citric Acid Solution", *Finn. Chem. Lett.*, pp. 233–236 (1974);

M. Kimura et al., "Kinetics and Mechanism of the Oxidation of L-Ascorbic Acid by Tris-(oxalato) Cobaltate(III) and Tris(1,10-phenanthroline)Iron(III) Complexes in Aqueous Solution", *J. Chem. Soc. Dalton Trans.*, pp. 423–427 (1982); and A. E. Martell, "Chelates of Ascorbic Acid, Formation and Catalytic Properties", *Ascorbic Acid Chemistry, Metabolism and Uses*, Chapter 7, P. A. Seib and B. M. Tolbert eds., Adv. in Chem. Series, ACS, Wash., D.C., pp. 153–178, (1982).

However, the ferric ion-based oxidation of ascorbic acid described above presents a definite disadvantage when used to eliminate ascorbic acid interference in an oxidase-peroxidase coupled reaction to assay for a predetermined analyte. In the oxidation of ascorbic acid, ferric ion is reduced to ferrous ion. Ferrous ion is a good reducing agent and can reduce an oxidized indicator dye, like tetramethylbenzidine (TMB), from its colored (oxidized) form to its colorless (reduced) form. Therefore, although the ferric ion eliminates the primary ascorbic acid interference, the ferrous ion then produces a secondary interfering affect that can result in an erroneously low assay result.

Accordingly, it would be extremely advantageous to provide a simple, accurate and trustworthy method of assaying a test sample for low levels of a predetermined analyte without the primary or secondary interfering affects attributed to ascorbic acid. Present day test strips for a predetermined analyte incorporate an indicator reagent composition including a suitable oxidase enzyme; peroxidase enzyme; and a metal ion complex to reduce primary ascorbate interferences. Although present day test strips used to assay for a predetermined analyte are stable and sensitive, present day test strips still need improvement in the area of sensitivity. Therefore, it would be a significant advance in the art of diagnostic assays if test strips were even more sensitive to a predetermined analyte in a test sample. It was towards achieving improvements in ascorbate resistance and sensitivity that the investigations resulting in the composition, device and method of the present invention were directed.

Surprisingly and unexpectedly, the composition and method of the present invention eliminate primary ascorbate interference and secondary interferences attributed to the metal ion or metal ion complex by including a cooxidant selected from the group consisting of bromate ion, chlorate ion, perchlorate ion, chromate ion, organic oxidants like a peroxide, a hydroperoxide or a N-halo compound, and combinations thereof, in the indicator reagent composition. To achieve the full advantage of the present invention, bromate ion is included in the indicator reagent composition as the cooxidant. It has been found that the cooxidant oxidizes the reduced form of the metal ion, e.g., ferrous ion, to the oxidized form, e.g., ferric ion, such that the reduced form of the metal ion is unavailable to interact with the oxidized form of the indicator dye. Therefore, the problem of decreased assay sensitivity attributed to a metal ion or a metal ion complex included in the indicator reagent composition is overcome.

Accordingly, a quantitative assay for a predetermined analyte can be performed by laboratory personnel to yield immediate and trustworthy test results by providing a more accurate assay method in an easy-to-use form, such as a dip-and-read test strip. In addition, the test strip method can be performed by an individual at home to more precisely monitor the level of a predetermined analyte, like glucose or occult blood, in a test sample, like blood or urine, or to monitor the success of the medical treatment the individual is undergoing.

As will be described more fully hereinafter, the method of the present invention allows the fast, accurate and trustworthy assay for a predetermined analyte by utilizing a test strip that includes a test pad comprising a suitable carrier matrix incorporating an indicator reagent composition of the present invention, said indicator reagent composition comprising an indicator dye, a redox mediator, a metal ion complex and a cooxidant. If the predetermined analyte, like glucose, is capable of interacting with an oxidase enzyme, the redox mediator comprises a suitable oxidase enzyme and a peroxidase enzyme. If the predetermined analyte, like occult blood, demonstrates peroxidative activity, the redox mediator comprises a hydroperoxide. The cooxidant is selected from the group consisting of bromate ion, chlorate ion, perchlorate ion, chromate ion, an organic oxidant like a peroxide, a hydroperoxide or a N-halo compound, and combinations thereof.

Prior to the present invention, no known method of assaying a test sample for a predetermined analyte in an oxidation-reduction coupled reaction included an indicator reagent composition comprising an indicator dye; a redox mediator; a metal ion complex; and a cooxidant selected from the group consisting of chlorate ion, bromate ion, perchlorate ion, chromate ion, an organic oxidant like a peroxide, a hydroperoxide or a N-halo compound, and combinations thereof. Although dry phase test strips including an indicator dye, a redox mediator and a metal ion complex have been used previously, dry phase test strips incorporating such compositions demonstrated a tendency to provide erroneous assay results because of secondary interferences attributed to the metal ion of the metal ion complex. Accordingly, such erroneous assays decreased the sensitivity of the test strip to the predetermined analyte in the test sample. In contrast, the indicator reagent composition of the present invention essentially eliminates both the primary ascorbate interference and, surprisingly and unexpectedly, the secondary interferences attributed to the metal ion complex. Consequently, the improved indicator reagent composition enhances the sensitivity of the assay, thereby providing a more accurate and trustworthy assay for a predetermined analyte by an oxidation-reduction based chemistry.

Several other attempts at achieving the above-mentioned goals of increased assay sensitivity and decreased ascorbate interference are found in prior patents and publications. For example, with regard to ascorbate interferences in glucose assays, methods have ranged from filtering the ascorbate from the test sample before the test sample contacts the test reagents to using an enzyme that interacts with the ascorbate. Accordingly, Canadian Patent No. 844,564 to Dahlquist disclosed a test device for glucose assays that includes a porous area to receive the test sample. The sample-receiving area does not include assay reagents, but comprises an ion exchange material that absorbs the ascorbate present in the test sample.

U.S. Pat. No. 4,168,205 to Danninger et al. described incorporating ascorbate oxidase into the test reagent formulation to enzymatically oxidize the ascorbate present in the sample to dehydroascorbate, a compound that does not adversely affect the assay. Japanese Patent Publication No. 55757 (1983) to Fuji Zoki Seiyaku K.K. disclosed pretreating a test sample with a metal chelate of a ligand, such as ethylenediaminetetraacetic acid or diethylenetriaminepentaacetic acid, to eliminate ascorbate, then assaying the test sample for cholesterol, glucose or uric acid.

Ku, in U.S. Pat. No. 3,411,887, described the elimination of ascorbate interference with reagent compositions that rely on enzymatic oxidizing substances, such as glucose oxidase, by using an ascorbate "trapping system." The "trapping system" utilizes a heavy metal ion that has an oxidation-reduction potential falling between a redox indicator dye and ascorbate. Suitable heavy metal compounds cited as examples include cobalt, iron, mercury and nickel. Another publication disclosing the complexing and oxidation of ascorbate using cobalt is G. Bragagnolo, *Ann. Chim. Applicata.*, 31, pp. 350–368 (1941), teaching that solutions of ascorbic acid were oxidized by air in the presence of cobalt metal. Also, similar activity has been reported for $Co(NH_3)_6Cl_3$ by T. Iwasaki, *Journal of the Chemical Society of Japan*, 63, pp. 820–826 (1942).

U.S. Pat. No. 4,310,626 to Burkhardt et al. described the use of ammonium cobalt(III) complexes to reduce ascorbate interference in assays for peroxidatively active substances. Burkhardt et al. disclose compositions comprising an organic hydroperoxide and a suitable indicator, such as 3,3',5,5'-tetramethylbenzidine, together with ammonium cobalt(III) complexes, such as $Co(NH_3)_6Cl_3$.

Copper ions also have been used to eliminate ascorbate interference from assays. For example, I. Pecht, et al., in "The Copper-Poly-L-Histidine Complex: I. The Environmental Effect of the Polyelectrolyte on the Oxidase Activity of Copper Ions", *J. Am. Chem. Soc.*, 89:1587 (1968), disclosed that ascorbate can be oxidized by oxygen and a copper catalyst. N. A. Vengerova et al. in the publication, "The Ascorbate-Oxidase Activity of the $Cu^{+2}$-Poly-4-Vinylpyridine Complex Alkylated with Bromoacetic Acid", *Vysokomol. soyed.*, A 13, No. 11, pp. 2509–2517 (1971) (translated by K. A. Allen), disclosed a method of synthesizing carboxymethyl derivatives of poly-4-vinylpyridine and taught that a Cu(II) polymer complex increases ascorbate oxidizing activity relative to copper ions alone. Other references relating to Cu(II) oxidation of ascorbate include: Z. Sun et al., "Studies on Functional Latices: Catalytic Effects of Histamine-Containing Polymer-latex-copper (II) Complex on the Oxidation of Ascorbic Acid", *Macromolecules*, 19:984–987 (1986); and Y. I. Skurlator et al., "The Mechanism of Ascorbic Acid Oxidation by Cu-(II)-Poly-4-Vinylpyridine Complexes", *European Polymer Journal*, 15:811–815 (1979).

U.S. Pat. No. 4,288,541 to Magers et al. disclosed the use of mercuric ion complexes, such as mercuric sarcosinate, to impart ascorbate resistance to a glucose oxidase-based assay for glucose. In addition to the above patents and publications, the problem of ascorbate interference in glucose assays is discussed in:

H. Gifford, et al., *J. Amer. Med. Assoc.*, 178, pp. 149–150 (1961);

P. O'Gorman, et al., *Brit. Med. J.*, pp. 603–606 (1960);

R. Brandt, et al., *Clin. Chem. Acta.*, 51, pp. 103–104 (1974); and

R. Brandt, et al., *Am. J. Clin. Pathol.*, 68, pp. 592–594 (1977).

Other methods of eliminating ascorbate interference in analytical determinations of predetermined analyte include, for example, West German Patent No. 29 07 628, directed to a wet phase urinalysis, whereby a urine sample is pretreated with an oxidant to remove ascorbate prior to the assay. The oxidants disclosed as useful are sodium iodate, sodium periodate, calcium hydrochlorite, potassium triiodide, sodium hydrochlorite, chloroamine and bromosuccinimide. Also, European Patent Application 0037056 described the use of iodate in diagnostic methods to avoid interference by reducing agents, including ascorbic acid.

U.S. Pat. No. 4,587,220, to Mayambala-Mwanika et al., disclosed the use of a chelated ferric ion to eliminate ascorbate interference in an assay for a peroxidatively active substance. Mayambala-Mwanika disclosed that a ferric chelate, like the ferric chelate of N-(2-hydroxyethyl)ethylenediaminetriacetic acid (Fe-HEDTA), eliminated ascorbate interference and did not produce a false positive test for a peroxidatively active compound.

Ismail et al., in U.S. Pat. No. 4,755,472, disclosed a stable test pad to assay for a peroxidatively active substance that includes a carrier matrix impregnated with 1,4-diisopropylbenzene dihydroperoxide and a benzidine indicator in a molar ratio of hydroperoxide to indicator of from about 0.9 to 3.0. A ferric chelate also can be included to provide ascorbate resistance. The test pad was stable during storage and does not lead to false positive tests on other test pads present on a multideterminant test strip, such as glucose test pad based on a peroxidase/potassium iodide indicator.

In contrast to the prior art, and in contrast to the presently-available commercial test strips, the composition, method and device of the present invention demonstrate increased sensitivity in an assay to detect or measure the concentration of a predetermined analyte in a test sample, wherein the predetermined analyte either is capable of interacting with an oxidase enzyme or demonstrates peroxidase activity. The method of the present invention utilizes an indicator reagent composition that a) effectively eliminates primary ascorbate interferences by including a metal ion complex, and b) effectively eliminates secondary interferences attributed to the metal ion complex by including a cooxidant selected from the group consisting of bromate ion, chlorate ion, perchlorate ion, chromate ion, organic oxidants like a peroxide, a hydroperoxide or a N-halo compound, and combinations thereof.

For example, bromate ion is used in analytical chemistry as a titrimetric reagent. In acidic media, bromate ion is almost as powerful an oxidizing agent as permanganate ion. In the presence of strong reducing agents, bromate ion ($BrO_3^-$) is reduced to bromide ion ($Br^-$). However, bromate ion is capable of oxidizing bromide ion to bromine ($Br_2$) as demonstrated in the following equations (1) and (2):

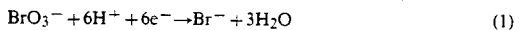

$$BrO_3^- + 6H^+ + 6e^- \rightarrow Br^- + 3H_2O \quad (1)$$

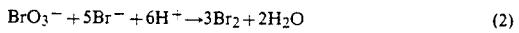

$$BrO_3^- + 5Br^- + 6H^+ \rightarrow 3Br_2 + 2H_2O \quad (2)$$

I. M. Kolthoff et al., in *Volumetric Analysis*, Vol. III, Titration Methods: Oxidation-Reduction Reactions, Chapter XII, Interscience Publishers, N.Y., N.Y. (1971), teach that bromide ion is formed in the first step of the reaction (Eq. 1), then the bromide ion reacts with excess bromate to yield free bromine (Eq. 2) in a pH-dependent reaction sequence. From Eqs. (1) and (2), it is demonstrated that acidic conditions are necessary for the reaction to proceed. Similarly, it is known that chlorate ion ($ClO_3^-$) does not demonstrate oxidizing properties in a neutral or alkaline solution, whereas chlorate ion demonstrates strong oxidizing properties in acidic solutions due to the presence of chloric acid ($HClO_3$).

The bromate ion oxidation of reduced metal ions also has been described. For example, the bromate ion oxidation of ferrous ion, i.e., iron(II), has been described in:

J. P. Birk, "Mechanism of the Bromate Ion Oxidation of Aquoiron(II)", *Inorg. Chem.*, 12, pp. 2468–2472 (1973);

J. P. Birk et al., "Mechanism of the Reduction of Bromate Ion by Cyano(bipyridyl) Iron(II) Complexes", *Inorg. Chem.*, 17, pp. 1186–1191 (1978); and S. G. Kozub, "Kinetics and Mechanisms of the Bromate Oxidations of Substitution—Inert Iron(II) Complexes in Acidic Aqueous Solution," Ph.D. Dissertation, Xerox University Microfilms, Ann Arbor, (1975).

In each above-identified publication, the reaction between bromate ion and ferrous ion was studied at very acidic conditions in perchloric acid. Furthermore, it is known that bromate ion does not oxidize ascorbic acid at an appreciable rate in the essentially neutral pH range of from 5 to 7.

U.S. patent application Ser. No. 337,620, filing date Apr. 13, 1989 and commonly assigned to the assignee of the present invention, describes the elimination of ascorbate interference from clinical assays by utilizing a copper(II) complex including a water-soluble polymer. In addition, a cooxidant is included to oxidize the copper(I) ion back to copper(II) after the interaction with ascorbate. The cooxidant can be an organic oxidant, like a peroxide or a N-halo compound, or an inorganic oxidant, like chromate, mercuric ion, thallium(III) ion, ceric(IV) ion, manganese(III) ion, bromate or iodate. U.S. patent application Ser. No. 337,620 does not teach or suggest any metal ion other than copper(II) as the oxidant to eliminate ascorbate interference.

As will be demonstrated more fully hereinafter, it has been found that a cooxidant selected from the group consisting of bromate ion, chlorate ion, perchlorate ion, chromate ion, organic oxidants like a peroxide, a hydroperoxide or a N-halo compound, and combinations thereof, when included in an indicator reagent composition of the present invention having an essentially neutral pH, oxidizes the reduced form of a metal ion, said metal ion included in the composition to eliminate primary ascorbate interference, back to the oxidized form of the metal ion. Such a result is both surprising and important. The result is surprising because of the pH range wherein the cooxidant, like bromate ion or chromate ion, oxidizes the metal; and the result is important because the metal ion, originally included in the composition to eliminate primary ascorbate interference, itself becomes a secondary interferent when the reduced form of the metal ion interacts with the colored, oxidized form of the indicator dye to reduce the dye to its colorless, reduced form. Accordingly, because of this secondary interference, the indicator dye apparently does not undergo a full color transition in response to the concentration of the predetermined analyte in the test sample. Therefore, an erroneously low assay result for the predetermined analyte is provided.

However, the composition, method and device of the present invention provide an accurate assay for a predetermined analyte that is capable of interacting with an oxidase enzyme or that exhibits peroxidase activity. Surprisingly, the method and composition of the present invention essentially eliminate both the primary and the secondary interferences attributed to ascorbate present in the test sample. Hence, in accordance with the method of the present invention, new and unexpected results are achieved in the dry phase test strip assay of blood, urine and other test samples for a predetermined analyte by utilizing an indicator reagent composition that includes a metal ion complex to eliminate primary ascorbate interference and a cooxidant selected from the group consisting of bromate ion, chlorate ion, perchlorate ion, chromate ion, organic oxidants like a peroxide, a hydroperoxide or a N-halo compound, and combinations thereof to eliminate secondary interferences attributed to the reduced form of the metal ion of the metal ion complex.

SUMMARY OF THE INVENTION

In brief, the present invention is directed to a new and improved composition, test device and method of determining the presence or concentration of a predetermined analyte in a test sample, wherein the predetermined analyte either a) is capable of interacting with an oxidase enzyme or b) demonstrates peroxidase activity. The device includes a test pad comprising a suitable carrier matrix incorporating an indicator reagent composition capable of interacting with the predetermined analyte to produce a detectable response. For home use, the indicator reagent composition produces a visually detectable response. For laboratory use, the indicator reagent composition produces a response that is detectable visually or by instrument. The carrier matrix of the test pad comprises a bibulous material, such as filter paper; a nonbibulous material, such as a layer or film of a polymerized material; or a combination thereof. An indicator reagent composition is incorporated into the carrier matrix, and the carrier matrix then holds the indicator reagent composition throughout the carrier matrix while maintaining carrier matrix penetrability by the predetermined analyte of the test sample.

More particularly, the present invention is directed to a method of assaying blood, urine or other liquid test samples for a predetermined analyte by utilizing a new and improved indicator reagent composition. The predetermined analyte is a compound capable of interacting with an oxidase enzyme, such as glucose, cholesterol, uric acid, alcohol or triglycerides; or a compound that demonstrates peroxidative activity, such as hemoglobin, i.e. occult blood. It has been demonstrated that an indicator reagent composition comprising: (a) an indicator dye, like a redox indicator, capable of undergoing a color transition in response to a predetermined analyte; (b) a redox mediator, either including an oxidase enzyme and peroxidase or including a hydroperoxide; (c) a metal ion complex; and (d) a cooxidant selected from the group consisting of bromate ion, chlorate ion, perchlorate ion, chromate ion, an organic oxidant like a peroxide, a hydroperoxide or a N-halo compound, and combinations thereof, has effectively eliminated both primary ascorbate interferences and secondary interferences attributed to the metal ion complex, and, therefore, has demonstrated an increased sensitivity to the predetermined analyte.

The metal ion complex included in the indicator reagent composition effectively eliminates the primary interfering affects of ascorbate present in the test sample by oxidizing the ascorbate. In this oxidation-reduction reaction, the metal ion of the metal ion complex is reduced. The cooxidant, like bromate ion, included in the composition then oxidizes the reduced form of the metal ion, such that the reduced form of the metal ion is not available to reduce the oxidized form of the indicator dye to its colorless reduced form. Accordingly, the color transition resulting from contact between the test pad incorporating the indicator reagent composition and the test sample is a true, not an apparent, color transition, and the color transition can be accurately correlated to the amount of predetermined analyte in the test sample.

In accordance with an important feature of the present invention, a more accurate and more reliable assay for a predetermined analyte in a liquid test sample is achieved because the interfering affects of ascorbate ion are eliminated by the metal ion complex, and the full color transition is detected because the cooxidant oxidizes the reduced form of the metal ion to the oxidized form of the metal ion before the reduced form of the metal ion can interact with the colored, oxidized form of the indicator dye. By utilizing the indicator reagent composition of the present invention in clinical test methods, the qualitative or quantitative assay for a predetermined analyte, such as glucose or hemoglobin, in urine or other test samples is more accurate because the full color transition of the indicator reagent composition in response to the amount of predetermined analyte in the test sample is detected. The color transition, and therefore the assay, is free of interferences attributed to ascorbate ion and to the reduced form of the metal ion present in the metal ion complex.

Therefore, one important aspect of the present invention to provide a simple, accurate and reproducible method of assaying blood, urine and other test samples for a predetermined analyte, wherein the predetermined analyte either is capable of interacting with an oxidase enzyme or is capable of exhibiting peroxidase activity. The method utilizes an indicator reagent composition that eliminates primary and secondary assay interferences attributed to ascorbate, and therefore provides increased sensitivity to the predetermined analyte.

The present method for assaying blood, urine or other test liquids for a predetermined analyte utilizes an indicator reagent composition comprising an indicator dye; a redox mediator either comprising a) an oxidase enzyme and peroxidase or b) a hydroperoxide; a metal ion complex; and a cooxidant selected from the group consisting of bromate ion, chlorate ion, perchlorate ion, chromate ion, an organic oxidant like a peroxide, a hydroperoxide or a N-halo compound, and combinations thereof wherein the primary interfering affects of ascorbate and the secondary interfering affects of the reduced form of the metal ion complex are essentially eliminated.

The indicator reagent composition, upon contact with a test sample, interacts with the predetermined analyte in the test sample and undergoes a detectable or measurable color transition to establish the presence or concentration of the predetermined analyte in the test sample. The composition, method and test device of the present invention provide an assay that is sensitive to low concentrations of the predetermined analyte and provide accurate assay results for the predetermined analyte.

BRIEF DESCRIPTION OF THE DRAWINGS

The above and other objects and advantages and novel features of the present invention will become apparent from the following detailed description of the preferred embodiments of the present invention in conjunction with the accompanying figures.

DETAILED DESCRIPTION OF THE INVENTION

Figure 1:
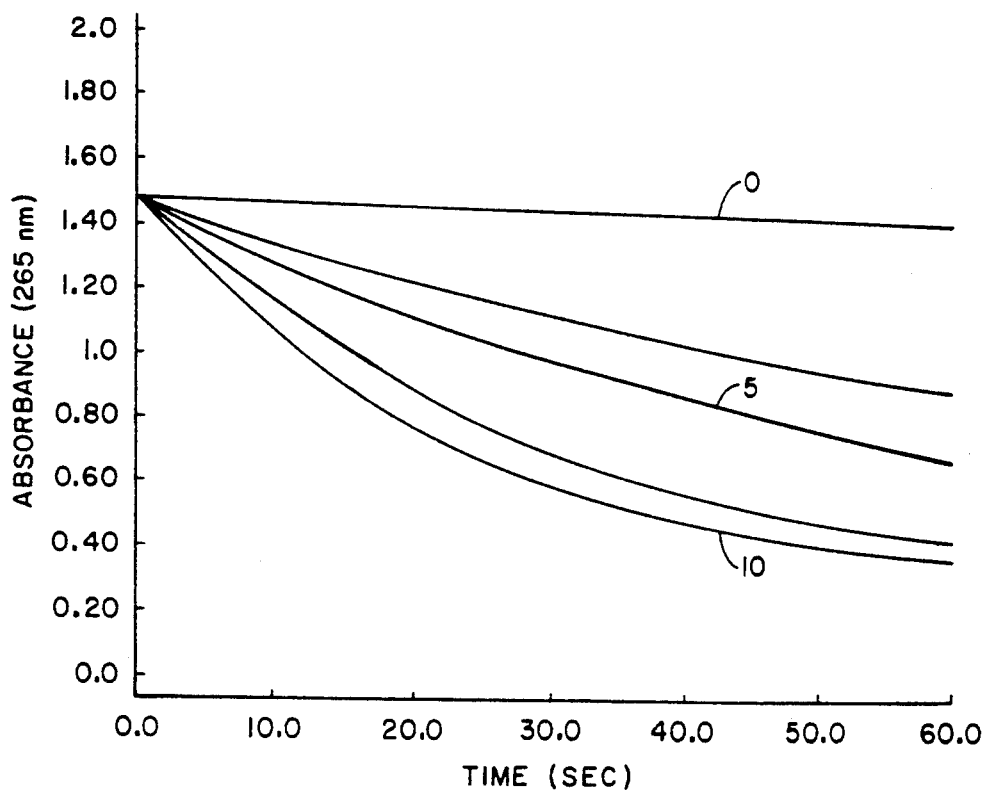
FIG. 1 is a series of plots of absorbance at 265 nm (nanometers) ($A_{265}$) vs. time (seconds) illustrating the increased rate of ascorbic acid oxidation by potassium bromate ($KBrO_3$) as monitored by the diminishing ascorbic acid peak at 265 nm, wherein the concentration range was varied from 0 mM to 10 mM (millimolar) $KBrO_3$ at pH 6.5 in the presence of 25 $\mu$M (micromolar) Fe(III)-HEDTA.

In accordance with the method of the present invention, the qualitative or quantitative assay for a predetermined analyte, such as glucose, cholesterol, uric acid or occult blood, in blood, urine and other test samples is accomplished by utilizing an indicator reagent composition comprising an indicator dye; a redox mediator; a metal ion complex; and a cooxidant selected from the group consisting of bromate ion, chlorate ion, perchlorate ion, chromate ion, an organic oxidant like a peroxide, a hydroperoxide or a N-halo compound, and combinations thereof. In accordance with an important feature of the present invention, the predetermined analyte is either (a) a compound capable of interacting with an oxidase enzyme, such as glucose, cholesterol, alcohol, uric acid or triglycerides, or (b) a compound that exhibits peroxidase activity, such as hemoglobin (i.e., occult blood) and myoglobin. Therefore, the redox mediator of the indicator reagent composition comprises, respectively, either (a) a suitable oxidase enzyme and peroxidase, or (b) a hydroperoxide.

The indicator reagent composition of the present invention essentially eliminates the primary interfering affects of ascorbic acid present in the test sample and the secondary interfering affects attributed to the metal ion complex that is included in the indicator reagent composition to interact with the ascorbic acid. Therefore, the indicator dye, after contacting a test sample including the predetermined analyte, undergoes a full color transition in response to an interaction between the predetermined analyte and the redox mediator.

The metal ion complex is included in the indicator reagent composition to oxidize ascorbic acid present in the test sample, and therefore to eliminate primary ascorbate interferences. U.S. Pat. No. 4,587,220 to Mayambala-Mwanika et al. discloses the use of particular ferric ion chelates to substantially eliminate primary ascorbate interferences. However, problems nevertheless still exist in present day methods and devices to assay for predetermined analytes capable of interacting with an oxidase enzyme or capable of exhibiting peroxidase activity. For example, in the oxidization of ascorbic acid, the metal ion of the metal ion complex is reduced, e.g., a ferric ion chelate is reduced to a ferrous ion chelate. Ferrous ion is a reducing agent of sufficient strength to interact with the oxidized form of the indicator dye, i.e., the colored form, to reduce the oxidized form of the dye to its reduced form, i.e., the colorless form. Therefore, an erroneously low assay results because a portion of the color transition is reversed.

Surprisingly and unexpectedly, it has been found that by including a suitable cooxidant, like bromate ion, in the indicator reagent composition, the ferrous ion is oxidized to ferric ion before the ferrous ion can interact with the oxidized form of the indicator dye, thereby precluding an interfering interaction between the ferrous ion and the oxidized indicator dye. Therefore, the color transition resulting from the interaction between the predetermined analyte and the indicator dye, mediated by the redox mediator, is more spectacular. Accordingly, the accuracy and the sensitivity of the assay to a low concentration of a predetermined analyte are increased.

The improved accuracy and increased sensitivity to low levels of a predetermined analyte afforded by the method of the present invention are especially useful in urine assays for glucose or for occult blood. A commercially-useful urine assay for a predetermined analyte includes a stable indicator reagent composition, is sensitive and preferably is resistant to primary ascorbic acid interference and secondary interferences attributed to ascorbic acid or to the elimination of ascorbic acid from the test sample.

As previously discussed, ascorbic acid and the ascorbate ion are common interferents in diagnostic tests based on redox indicator dyes. Ascorbic acid interference in the assay of urine for glucose and occult blood is well known in the art and preferably is eliminated. Ascorbic acid interferes with the oxidation of the indicator dye, and therefore ascorbic acid in a test sample produces an apparent negative result for a predetermined analyte. "Ascorbate resistance" therefore is defined as a negligible interference with the color transition of the indicator dye when a urine sample contains as much as about 200 mg (milligrams) ascorbic acid per deciliter (dL) of sample.

The elimination of ascorbate interference in the assay for a predetermined analyte is clinically important because detecting a low concentration of the predetermined analyte in the test sample can signify a diseased or damaged condition that should be investigated further. Accordingly, and as will be discussed more fully hereinafter, the method and device of the present invention accurately assay for a low concentration of a predetermined analyte in a test sample. The method and device of the present invention utilize an indicator reagent composition that undergoes a color transition only in response to the concentration of the predetermined analyte in the test sample, thereby providing a sensitive and reliable assay for a predetermined analyte. Surprisingly and unexpectedly, it has been found that including a suitable cooxidant in an indicator reagent composition further comprising an indicator dye, a redox mediator and a metal ion complex substantially increases the accuracy and sensitivity of the assay for a predetermined analyte by essentially eliminating the primary interfering affects attributed to ascorbate ion and the secondary interfering affects attributed to metal ions present in a reduced form.

It will become apparent that the method and device of the present invention also can be used to determine the presence or quantitive concentration of a predetermined analyte in blood plasma or serum, urine, feces, and gastrointestinal contents; and more generally, the predetermined analyte concentration of many other biological fluids and semisolids as well. In general, any aqueous test sample, or test sample that is soluble in an aqueous solvent, can be assayed. To achieve the full advantage of the present invention, the composition of the present invention is employed in a dry phase test strip to determine the presence or concentration of a predetermined analyte in urine or other test samples, wherein the predetermined analyte either is capable of interacting with an oxidase enzyme or is capable of exhibiting peroxidase activity.

The method and test device utilizing the composition of the present invention provide a more accurate, trustworthy and clinically significant assay for a predetermined analyte because the indicator dye is oxidized to undergo a color transition in response to the amount of the peroxidatively active substance present in the test sample. The degree and intensity of the color transition are not diminished due to the presence of ascorbic acid or to the presence of reduced metal ions, both of which reduce the colored, oxidized form of the indicator dye to its colorless, reduced form. Accordingly, assay sensitivity is increased, and a fast, accurate and trustworthy method of assaying for a predetermined analyte, performable at home or in the laboratory to yield essentially immediate assay results, is achieved.

The method of the present invention utilizes the ability of a predetermined analyte either to interact with an oxidase enzyme to generate hydrogen peroxide, that in turn interacts with a peroxidase to release oxygen, or to interact with a hydroperoxide to release oxygen. In either case, the oxygen then oxidizes an indicator dye. The oxidation of the indicator dye results in a color transition of the indicator reagent composition, with the degree and intensity of the color transition being directly proportional to the concentration of the predetermined analyte in the test sample. Accordingly, the indicator reagent composition of the present invention includes a redox mediator, i.e., either an a) oxidase enzyme and peroxidase or b) a hydroperoxide, and an indicator dye, wherein the indicator dye undergoes a color transition upon conversion to its oxidized form by oxygen formed from an interaction between the redox mediator and a predetermined analyte present in the test sample.

The indicator reagent composition also includes a compound to eliminate primary ascorbate interference from the assay for the predetermined analyte. In accordance with the present invention, the ingredient included to eliminate ascorbate interference preferably is a metal ion complex. However, as will be discussed more fully hereinafter, a water-soluble metal ion salt also can be used to eliminate the primary ascorbate interference. The metal ion is present in its oxidized form, such as ferric ion, for example, and is capable of interacting with, and oxidizing, ascorbate to eliminate ascorbate interference. Consequently, the metal ion is reduced to its reduced form, i.e. ferrous ion. The ferrous ion however can interact with the colored, oxidized form of the indicator dye to regenerate ferric ion and the colorless, reduced form of the indicator dye. Therefore, a portion of the color transition is reversed and an erroneously low assay results.

Consequently, and in accordance with an important feature of the present invention, the indicator reagent composition also includes a cooxidant selected from the group consisting of bromate ion ($BrO_3^-$), chlorate ion ($ClO_3^-$), perchlorate ion ($ClO_4^-$), chromate ion ($CrO_4^{-2}$), an organic oxidant like a peroxide, a hydroperoxide or a N-halo compound, and combinations thereof to effectively and rapidly reoxidize the ferrous ion to ferric ion, thereby precluding an interaction between the ferrous ion and the oxidized form of the indicator dye. Therefore, the full color transition is detected and measured to provide an accurate and reliable assay for a predetermined analyte.

As will be discussed more fully hereinafter, the indicator reagent composition of the present invention also can include a buffer compound to provide a pH in the range of from about 5 to about 7. Within this pH range, the color transition resulting from oxidation of the indicator dye is the most spectacular and differentiable. However, it is unexpected for bromate ion, chlorate ion or perchlorate ion to interact with a reduced metal ion at this slightly acidic to essentially neutral pH to regenerate the oxidized form of the metal ion and to generate an innocuous reduction product, like bromide ion. The prior art teaches that bromate ion, chlorate ion and perchlorate ion act as oxidizing agents in very acidic media, such as media having a pH of below about 4.

The following unbalanced reactions illustrate and summarize the interactions that occur when a test sample including a predetermined analyte contacts a test device including an indicator reagent composition of the present invention. For illustration purposes, the predetermined analyte is glucose; the metal ion complex is the of ferric ion chelate N-(2-hydroxyethyl)ethylenediaminetetraacetic acid (Fe(III)-HEDTA); and the cooxidant is bromate ion. The term "Ind. dye" refers to an indicator dye, and the terms "ox" and "red" are abbreviations for the oxidized form and the reduced form of the dye. Fe(II)-HEDTA is the reduced form, or ferrous form, of Fe(III)-HEDTA.

Glucose + Oxygen ($O_2$) ⟶ (3)
Hydrogen Peroxide ($H_2O_2$) + Gluconic Acid

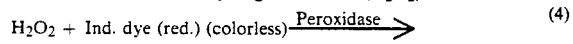
$H_2O_2$ + Ind. dye (red.) (colorless) —Peroxidase→ (4)
Ind. dye (ox.) (colored) + $H_2O$

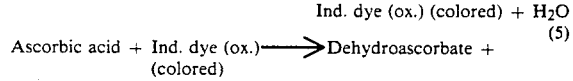
Ascorbic acid + Ind. dye (ox.) ⟶ Dehydroascorbate + (5)
(colored)
Ind. dye (red.)
(colorless)

Fe(III)-HEDTA + Ascorbic Acid ⟶ (6)
Fe(II)-HEDTA + Dehydroascorbate

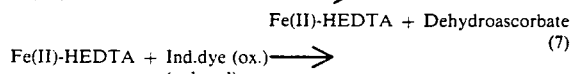
Fe(II)-HEDTA + Ind.dye (ox.) ⟶ (7)
(colored)
Fe(III)-HEDTA + Ind. dye (red.)
(colorless)

Bromate ($BrO_3^-$) + Fe(II)-HEDTA ⟶ (8)
Bromide ($Br^-$) + Fe(III)-HEDTA Equations (3) and (4) illustrate the reaction scheme for the chromogenic assay for glucose, wherein the degree and intensity of the color change occurring in Equation (4) are proportional to the amount of glucose in the test sample. Equation (5) illustrates ascorbic acid interacting with the oxidized indicator dye to diminish the color transition and provide a false negative assay result or otherwise interfere with the assay. Equation (6) shows the ferric ion chelate, Fe(III)-HEDTA, eliminating the primary ascorbate interference by oxidizing ascorbic acid to the innocuous dehydroascorbate. Equation (7) illustrates the secondary ascorbate interference that results when the reduced form of the metal ion complex (Fe(II)-HEDTA) interacts with the oxidized form of the indicator dye to provide the reduced form of the indicator dye, and therefore diminish the degree and intensity of the color transition. Equation (8) illustrates bromate ion interacting with the ferrous ion of reduced form of the metal iron complex (Fe(II)-HEDTA) to eliminate secondary ascorbate interferences. Equation (8) shows that bromate ion is reduced to the innocuous bromide ion and that the noninterfering Fe(III)-HEDTA is regenerated. Accordingly, by including a metal ion complex and a suitable cooxidant, like bromate ion, in the indicator reagent composition, interferences attributed to ascorbate (primary interference) and to the metal ion complex added to eliminate ascorbate (secondary interference) are essentially eliminated.

The indicator dye included in the indicator reagent composition is limited only in that the indicator dye is capable of undergoing a detectable response, and preferably a chromogenic response, in the presence of a predetermined analyte and a redox mediator, such as an oxidase-peroxidase couple or a hydroperoxide. Accordingly, the indicator dye preferably is a redox indicator that undergoes a color transition upon conversion from its reduced form to its oxidized form by the interaction between the predetermined analyte and the redox mediator. The indicator dye should be sufficiently stable such that both a predetermined analyte and a redox mediator are present before a color transition occurs. To achieve the full advantage of the present invention, the indicator dye undergoes a color transition through various detectable and measurable degrees and intensities of color such that the degree and intensity of the color transition can be correlated to the concentration of a predetermined analyte in a test sample.

Several indicator dyes are suitable for use in the composition of the present invention, and generally include compounds that are oxidized relatively easily to yield deeply-colored oxidation products. Suitable classes of indicator dyes include, but are not limited to, the benzidine-type indicator compounds and the heterocyclic azine indicator compounds. Examples of the heterocyclic azine indicator compounds include, but are not limited to, bis-(N-ethylquinol-2-one)-azine and (N-methylbenzthiazol- 2-one)-(1-ethyl-3-phenyl-5-methyl-triazol-2-one)-azine. The benzidine-type indicator compounds include, but are not limited to, for example, benzidine, o-tolidine; 3,3',5,5'-tetra(lower alkyl)benzidine; o-dianisidine; 2,7-diaminofluorene; and mixtures of these and other suitable indicator dyes. The expression "lower alkyl", as used above, is defined as an alkyl moiety having from one to about six carbon atoms, including methyl, ethyl, n-propyl, isopropyl and the various butyl, pentyl and hexyl isomers. To achieve the full advantage of the present invention, the redox indicator, 3,3',5,5'-tetramethylbenzidine (TMB), is included in the indicator reagent composition.

The indicator dye usually is present in the indicator reagent composition in a concentration of from about 5 mM (millimolar, or millimoles of indicator dye per liter of indicator reagent composition) to about 60 mM, and preferably in a concentration of from about 20 mM to about 40 mM. It should be understood that the amount of indicator dye in the indicator reagent composition can be less than about 5 mM, or greater than about 60 mM, depending upon the intensity of the color transition that a particular indicator dye undergoes upon oxidation. In general, the amount of indicator dye included in the indicator reagent composition is limited only in that the indicator dye undergoes a detectable color transition for a qualitative assay or, for a quantitative assay, undergoes a measurable color transition in proportion to the amount of predetermined analyte in the test sample.

In accordance with another important feature of the present invention, the indicator reagent composition also includes a redox mediator. If the predetermined analyte is a compound capable of interacting with an oxidase enzyme, then the redox mediator includes a) an oxidase enzyme that specifically interacts with the predetermined analyte and b) peroxidase enzyme. If the predetermined analyte is a compound capable of exhibiting peroxidase activity, then the redox mediator includes a hydroperoxide.

In the assay for a predetermined analyte that exhibits peroxidative activity, like hemoglobin, the predetermined analyte is capable of interacting with a redox mediator comprising a hydroperoxide. As a result of this interaction, the indicator dye is oxidized and undergoes a color transition proportional to the amount of predetermined analyte in the test sample. If the predetermined analyte present in the test sample exhibits peroxidative activity, i.e., behaves similar to the enzyme peroxidase, the predetermined analyte catalyzes the oxidation of the indicator dye.

Accordingly, a hydroperoxide included in the indicator reagent composition of the present invention as a redox mediator for a predetermined analyte that exhibits peroxidative activity should be sufficiently stable such that free oxygen is not liberated in the absence of the predetermined analyte. In addition, the hydroperoxide should possess a sufficiently low vapor pressure such that the hydroperoxide does not evaporate, or sublime, from the indicator reagent composition during storage, or after the indicator reagent composition is incorporated into a carrier matrix of a test pad of a dry phase test strip. Furthermore, the hydroperoxide should demonstrate a sufficient sensitivity to detect 1 part of the predetermined analyte, like hemoglobin, in one trillion parts of test sample, such as in the assay of urine for occult blood.

Therefore, a hydroperoxide useful in the indicator reagent composition of the present invention is selected from among the many well known hydroperoxides. A suitable hydroperoxide is capable of interacting with a predetermined analyte in the presence of a suitable indicator dye to produce a detectable response, such as a color transition or a change in the amount of light absorbed or reflected by the test sample. Organic hydroperoxides are preferred. Specific examples of suitable hydroperoxides include, but are not limited to, cumene hydroperoxide; t-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene monohydroperoxide; p-t-butylisopropylbenzene hydroperoxide; 2-($\alpha$-hydroperoxyisopropyl)-6-isopropylnaphthalene; tetralin hydroperoxide and combinations thereof. In the assay of urine for occult blood, 1,4-diisopropylbenzene dihydroperoxide (DBDH) is the preferred hydroperoxide because of the stability, sensitivity, and nonvolatility of DBDH.

The concentration of a hydroperoxide included in the indicator reagent composition ranges from about 5 mM to about 100 mM, and preferably from about 25 mM to about 75 mM. The specific amount of a particular hydroperoxide included in the indicator reagent composition is dependent upon the physical and chemical properties of the particular hydroperoxide, such as volatility, stability and sensitivity towards a predetermined analyte that exhibits peroxidative activity.

In the assay for a predetermined analyte capable of interacting with an oxidase enzyme, like glucose or cholesterol, the redox mediator includes a) an oxidase enzyme that specifically interacts with the predetermined analyte and b) a peroxidase enzyme. In this assay, the predetermined analyte and the oxidase enzyme first interact to generate hydrogen peroxide, then the hydrogen peroxide and the peroxidase enzyme interact to oxidize the indicator dye to cause a color transition of the indicator reagent composition, wherein the degree and intensity of the color transition are correlated to the amount of predetermined analyte in the test sample. As a result, a method of assaying for a particular predetermined analyte can be designed by utilizing a redox mediator including the appropriate oxidase enzyme and peroxidase enzyme.

Accordingly, the oxidase enzyme included in the indicator reagent composition is capable of selectively interacting with the predetermined analyte of interest as opposed to other constituents of the test sample. For example, in the assay for glucose, glucose oxidase is included as the oxidase enzyme; and in the assay for cholesterol, cholesterol oxidase is included as the oxidase enzyme. However, in addition to glucose oxidase and cholesterol oxidase, other oxidase enzymes that interact with a particular predetermined analyte to generate oxidizing capability to oxidize the indicator dye include, but are not limited to:

uricase,
aryl-alcohol oxidase,
L-gluconolactone oxidase,
galactose oxidase,
pyranose oxidase,
L-sorbase oxidase,
pyridoxin 4-oxidase,
alcohol oxidase,
L-2-hydroxyacid oxidase,
pyruvate oxidase,
oxalate oxidase,
glyoxylate oxidase,
dihydro-orotate oxidase,
lathosterol oxidase,
choline oxidase,
glycolate oxidase,
glycerol-3-phosphate oxidase,
xanthine oxidase,
sarcosine oxidase,
N-methylamino-acid oxidase,
$N^6$-methyl-lysine oxidase,
6-hydroxy-L-nicotine oxidase,
6-hydroxy-D-nicotine oxidase,
nitroethane oxidase,
sulphite oxidase,
thiol oxidase,
cytochrome c oxidase,
Pseudomonas cytochrome oxidase,
ascorbate oxidase,
o-aminophenol oxidase, and
3-hydroxyanthranilate oxidase.

Such oxidase enzymes can be used in the assay for a variety of predetermined analytes such as triglycerides, uric acid, glucose, cholesterol and galactose.

The concentration of the oxidase enzyme included in the indicator reagent composition is sufficient to interact with the entire amount of predetermined analyte in the test sample. Generally, therefore, the amount of oxidase enzyme included in the indicator reagent composition is in the range of from about 50 units to about about 1000 units, and preferably in the range of from about 50 units to about 250 units, per milliliter (mL) of indicator reagent composition, wherein one unit is defined as the amount of oxidase enzyme to oxidize 1.0 μmole (micromole) of substrate per minute at the appropriate pH for the assay of interest and at a temperature of about 30° C. It should be understood that the amount of oxidase enzyme in the indicator reagent composition can be greater than 1000 units per mL or less than 50 units per mL depending upon the particular predetermined analyte of interest and the expected concentration of that particular predetermined analyte in the test sample.

Similarly, the amount of peroxidase enzyme in the indicator reagent composition is sufficient to interact with the entire amount of hydrogen peroxide generated in the interaction between the oxidase enzyme and the predetermined analyte. Generally, therefore, the amount of peroxidase enzyme included in the indicator reagent composition is in the range of about 50 units to about 1000 units, and preferably, in the range of from about 50 units to about 250 units, per mL of indicator reagent composition, wherein one unit is defined as the amount to form 1 mg (milligram) of purpurogallin from pyrogallol in 20 seconds at pH 6.0 at 20° C. It also should be understood that the amount of peroxidase enzyme can be greater than 1000 units per mL or less than 50 units per mL depending upon the particular predetermined analyte of interest and the expected concentration of that particular predetermined analyte in the test sample.

Furthermore, in addition to the indicator dye and the redox mediator, the indicator reagent composition also includes a metal ion complex to impart ascorbate resistance to the assay. In general, the metal ion complex facilitates oxidation of the ascorbate present in the test sample by the metal ion and thereby eliminates the ascorbate interference. If the ascorbate acid is not oxidized, the ascorbic can interact with the colored, oxidized form of the indicator dye to provide oxidized ascorbic acid and the colorless, reduced form of the indicator dye. Accordingly, an erroneously low or a false negative assay for the predetermined analyte results. Generally, the metal ions are included in the indicator reagent composition as a metal ion complex to increase the solubility of the metal ion and to help overcome the inherent peroxidative activity of metal ions. However, a water-soluble salt of a metal ion also can be included in the indicator reagent composition.

In accordance with an important feature of the present invention, it is envisioned that essentially any metal ion, when complexed, capable of oxidizing ascorbic acid rapidly to eliminate ascorbate interference can be included in the indicator reagent composition of the present invention. Accordingly, a metal ion useful in the metal ion complex included in the indicator reagent composition is selected from the group consisting of ferric ion, cupric ion, mercuric ion, stannic ion, nickel-(II) ion, manganese(III) ion, cadmium(II) ion, zinc(II) ion, molybdenum(V) ion, chromium(IV) ion, vanadium(III) ion, ceric(IV) ion and combinations thereof. In addition, other metal ions having a valence state greater than (III) also can be used as the metal ion of the metal ion complex. To achieve the full advantage of the present invention, the metal ion present in the metal ion complex is the ferric ion.

As stated above, the metal ion is complexed to increase the water solubility of the metal ion and to reduce the inherent peroxidative activity of the metal ion. However, the identity of the complexing agent is not particularly limited and, for example, can include a polycarboxyalkylamine, like ethylenediaminetetraacetic acid or nitrilotriacetic acid; a polycarboxylic acid or salt, like citric acid, oxalic acid, tartaric acid or gluconic acid; a polyhydroxy compound, like sorbitol; a lignosulfonate; a glucoheptonate; bis(dimethylglyoximato); salicylate complexes, like bissalicylaldehydeethylenediiminato; dithioate derivatives; polyethyleneamines, like triethyleneamine; a 2,4-pentanedione derivative; a dipyridine derivative; triethylenepyridine amine; a polypeptide containing cysteine, glycine or histidine; a proline derivative; a thiocrown ether, like 1,4,8,11,22,25-octathiacyclooctosane; a triphenylphosphine; or combinations thereof.

In particular, ferric ion complexes useful in the indicator reagent composition include, but are not limited to, the ferric ion polycarboxyalkylamine chelates, such as the ferric ion chelates of N-(2-hydroxyethyl)ethylenediaminetriacetic acid (Fe-HEDTA), ethylenediaminetetraacetic acid (Fe-EDTA), cyclohexylenediaminetetraacetic acid (Fe-CDTA), nitrilotriacetic acid (Fe-NTA), iminodiacetic acid (Fe-IMDA), ethylenediamined:acetic dipropionic acid (Fe-EDDP both α and β forms), hydroxyethyliminodiacetic acid (Fe-HIMDA), diethylenetriaminepentaacetic acid (Fe-DTPA), ethylenebis(oxyethylenenitrilo)tetracetic acid (Fe-EGTA), N-(2-acetamido)iminodiacetic acid (Fe-ADA), or combinations thereof. The ferric ion polycarboxyalkylamine chelates are described more fully in U.S. Pat. No. 4,587,220, hereby incorporated by reference. Other suitable ferric ion complexes include ferric citrate, ferric gluconate, ferric glucoheptonate, ferric bissalicylaldehydeethylenediiminato, and ferric triethylenepyridine amine. The preferred ferric ion complexes are Fe-HEDTA and Fe-EDTA. To achieve the full advantage of the present invention, the ferric ion chelate Fe-HEDTA is included in the indicator reagent composition of the present invention. It should be understood however that the metal ion also can be present in an uncomplexed form, such as a water-soluble salt. For example, and as will be demonstrated more fully hereinafter, mercuric nitrate has been utilized as the metal ion in an uncomplexed form.

The metal ion complex is included in the indicator reagent composition in an amount ranging from about 0.5 mM to about 50 mM, and preferably in the range of from about 1 mM to about 25 mM. When present in this amount, the metal ion complex essentially eliminates primary ascorbate interference in the assay of test samples including up to about 200 mg/dL (milligrams per deciliter) ascorbate. In addition, it should be understood that a suitable metal ion complex, like Fe(III)-HEDTA, or a suitable metal salt, like mercuric nitrate, can be commercially available, and therefore incorporated directly into the indicator reagent composition. Alternatively, the metal ion complex can be produced in situ during manufacture of the indicator reagent composition, such as by independently incorporating a metal ion salt, like ferric chloride hexahydrate (FeCl$_3$·6H$_2$O), and an approximately equimolar amount of a complexing agent, like N-(2-hydroxyethyl)ethylenediaminetriacetic acid (HEDTA), into the indicator reagent composition to form the Fe-HEDTA ferric ion chelate.

When a composition including only an indicator dye, a redox mediator and a metal ion complex is used in a method to assay a test sample for a predetermined analyte definite disadvantages become apparent. As previously stated, the redox mediator is included in the composition to interact with the predetermined analyte for the oxidation of the indicator dye. The metal ion complex is included in the composition to eliminate primary ascorbate interference from the assay. However, in eliminating ascorbate interference by oxidizing the ascorbate, the metal ion is reduced. This reduced form of the metal ion can interact with the colored, oxidized form of the indicator dye that results from the predetermined analyte-redox mediator interaction. The reduced form of the metal ion reduces the oxidized form of the indicator dye to the colorless, reduced form of the indicator dye, thereby diminishing the degree and intensity of the color transition and providing an erroneously low assay result for the predetermined analyte.

Accordingly, the reduction of the oxidized indicator dye by the reduced form of the metal ions introduces a severe limitation on the sensitivity of a dry phase test strip in the assay for a predetermined analyte. As will be demonstrated more fully hereinafter however, dry phase test strips incorporating an indicator dye, a redox mediator, a metal ion complex and a cooxidant selected from the group consisting of bromate ion, chlorate ion, perchlorate ion, chromate ion, an organic oxidant like a peroxide, a hydroperoxide or a N-halo compound, and combinations thereof overcome the erroneously low assay results previously observed in an assay for a predetermined analyte.

Surprisingly and unexpectedly, it has been found that including a suitable cooxidant in an indicator reagent composition that further includes an indicator dye, a redox mediator and a metal ion complex sufficiently oxidizes the reduced form of the metal ion such that the oxidized indicator dye is not reduced to its colorless, reduced form by the reduced form of the metal ion. In general, bromate ion, chlorate ion or perchlorate ion, chromate ion, an organic oxidant like a peroxide, a hydroperoxide or a N-halo compound, or a combination thereof, is a suitable cooxidant, and is included in the indicator reagent composition of the present invention as a water soluble salt or water-soluble compound.

Therefore, for example, the bromate ion is included in the indicator reagent composition as: a) a bromate salt having a counter cation such as potassium, sodium, lithium, calcium, magnesium, ammonium, an alkylammonium, a hydroxyalkylammonium, an alkylphosphonium or a combination thereof, wherein the alkyl or hydroxyalkyl group includes from one to about six carbon atoms, in order to provide a sufficiently water-soluble bromate salt if an aqueous media is desired, or b) a bromate salt having a counter cation such as quaternary alkylammonium, cyanine, pyridinium, picolinium, quinalkinium, quinolinium, quaternary alkyl phosphonium or combinations thereof, wherein the alkyl group includes six or more carbon atoms in order to provide a sufficiently water-insoluble bromate salt if a nonaqueous media is desired. Similar counter cations of chlorate, perchlorate and chromate salts also can be used as the cooxidant, as long as the cation does not adversely affect the assay for the predetermined analyte. To achieve the full advantage of the present invention, bromate ion is included in the indicator reagent composition in the form of potassium bromate.

The cooxidant also can be an organic oxidant, like a peroxide, a hydroperoxide or a N-halo compound. Examples of peroxides and hydroperoxides include, but are not limited to, diisopropylbenzene hydroperoxide (DBDH), diisopropylbenzene monohydroperoxide, phenylcyclohexane hydroperoxide, p-(α-hydroperoxyisopropyl)benzoic acid, p-(bromoisopropyl)benzene hydroperoxide and p-(α-hydroxy-α'-hydroperoxyisopropyl)benzene. DBDH is the preferred peroxide or hydroperoxide. A nonlimiting example of an organic N-halo compound is a 1-halobenzotriazole, wherein the halo atom preferably is chloro.

In general, the cooxidant is included in the indicator reagent composition in a concentration ranging from about 5 mM to about 100 mM, and preferably in a concentration ranging from about 20 mM to about 70 mM. To achieve the full advantage of the present invention, the cooxidant is bromate ion and is included in the indicator reagent composition in a concentration ranging from about 40 mM to about 60 mM. Within the above concentration range, a sufficient amount of cooxidant is present in the indicator reagent composition to oxidize the reduced form of the metal ion back to its oxidized form.

An indicator reagent composition of the present invention, including a cooxidant, allows for the accurate and sensitive assay of a predetermined analyte. The metal ion complex, such as Fe(III)-HEDTA, accomplishes the rapid two-electron oxidation of ascorbic acid to eliminate ascorbic acid as an interferent in the assay. The oxidation of ascorbic acid is illustrated in the balanced reaction of Equation 10, wherein Fe(III)-HEDTA and Fe(II)-HEDTA are the ferric and ferrous chelates of N-(2-hydroxyethyl)ethylenediaminetetraacetic acid (HEDTA), respectively.

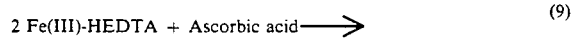

$$2\, Fe(III)\text{-HEDTA} + \text{Ascorbic acid} \longrightarrow \qquad (9)$$

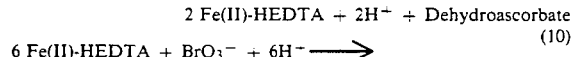

$$2\, Fe(II)\text{-HEDTA} + 2H^+ + \text{Dehydroascorbate}$$

$$6\, Fe(II)\text{-HEDTA} + BrO_3^- + 6H^+ \longrightarrow \qquad (10)$$

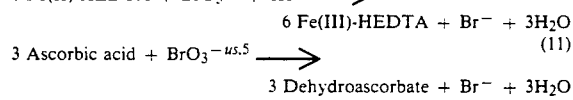

$$6\, Fe(III)\text{-HEDTA} + Br^- + 3H_2O$$

$$3\, \text{Ascorbic acid} + BrO_3^- \longrightarrow \qquad (11)$$

$$3\, \text{Dehydroascorbate} + Br^- + 3H_2O$$

Surprisingly, the bromate ion, at a pH of from about 5 to about 7, then oxidizes the reduced metal ion of the metal ion complex from its lower valence state (Fe(II)-HEDTA) to its higher valence state (Fe(III)-HEDTA), thereby precluding an oxidation-reduction interaction between the reduced metal ion and the oxidized indicator dye. This interaction between bromate ion and Fe(II)-HEDTA is illustrated in the balanced reaction of Equation 10.

The stoichiometry of Equation 10 was determined in a qualitative titration experiment by adding known amounts of potassium bromate to a solution including a known amount of ferrous ion buffered at pH 6.5. O-phenanthroline was used to detect remaining Fe(II) (ferrous) ion. The results of the titration experiments are illustrated in TABLE I. In general, the Fe(II)-containing solution remained o-phenanthroline reactive until the amount of potassium bromate added to the solution reached an equivalent ratio of one. In each qualitative titration, bromine (Br$_2$) was not detected by an analytical method capable of detecting as little as 10 μM (micromolar) bromine. The reduction product of bromate-ferrous ion interaction under the above conditions therefore has been theorized to be bromide ion (Br$^-$). From TABLE I, it is seen that the equivalent weight of potassium bromate therefore is one-sixth of its molecular weight, showing a change of bromine from the +5 oxidation state (BrO$_3^-$) to the −1 oxidation state (Br$^-$). Accordingly, from TABLE I and Equation 10, to achieve the full advantage of the present invention, the molar amount of bromate ion included in the indicator reagent composition is at least one-sixth of the molar amount of the Fe(III)-HEDTA included in the composition. The overall reaction between Fe(III)-HEDTA, ascorbic acid and bromate ion is illustrated in the balanced reaction of Equation 11.

TABLE I

Oxidation of Fe(II)-HEDTA by KBrO$_3$
Determination of Stoichiometry
Buffer: 0.5M citrate pH 6.5
Initial Fe(II)-HEDTA concentration: 10 mM

| Experiment No. | Conc. of Added KBrO$_3$, mM | Ratio Meq. KBrO$_3$ to Meq. Fe(II) | Color upon addition of o-phenanthroline |
|---|---|---|---|
| 1 | 0 | 0 | Red |
| 2 | 0.33 | 0.2 | Red |
| 3 | 0.67 | 0.4 | Red |
| 4 | 1.0 | 0.6 | Red |
| 5 | 1.33 | 0.8 | Red |
| 6 | 1.67 | 1.0 | No red |
| 7 | 3.33 | 2.0 | No red |

Such results are unexpected because bromate ion exhibits its oxidizing strength in low pH media, whereas the assay for a predetermined analyte normally is conducted in the essentially neutral pH range of from about 5 to about 7. Furthermore, it has been found that bromate ion does not oxidize the indicator dye to provide a false positive or an erroneously high assay result; does not interfere with the interaction between the predetermined analyte and the redox mediator; exhibits a sufficiently fast reaction rate with the reduced form of the metal ion; operates at the neutral pH range necessary for enzymatic interactions; and is reduced to the innocuous bromide ion (Br$^-$) as opposed to the highly-colored bromine molecule (Br$_2$) that interferes with the colorimetric response of the indicator reagent composition.

In accordance with another important feature of the present invention it has been found that the concentration of the metal ion complex and the concentration of the cooxidant in the indicator reagent compositions affects the rate of ascorbic acid oxidation. For example, the rate of ascorbic acid oxidation of an aqueous solution that was 0.1 mM (millimolar) in ascorbic acid, 25 μM (micromolar) in Fe(III)-HEDTA and a variable amount of potassium bromate, and having a buffer pH of 6.5, was determined by following the decrease in absorbance at 265 nm (nanometers).

Figure 2:
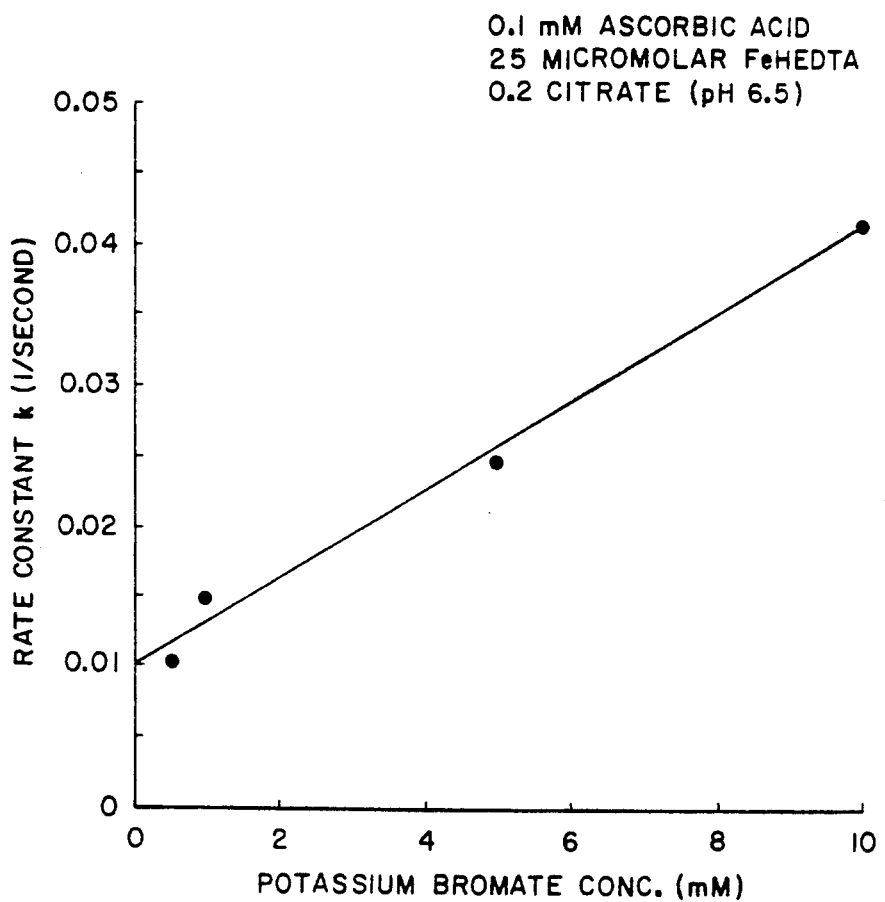
FIG. 2 is a graph of the rate constant of ascorbic acid oxidation, (k (sec$^{-1}$)) vs. potassium bromate over the concentration range of 0 mM to 10 mM $KBrO_3$ at pH 6.5 and in the presence of 25 $\mu$M Fe(III)-HEDTA.
Figure 3:
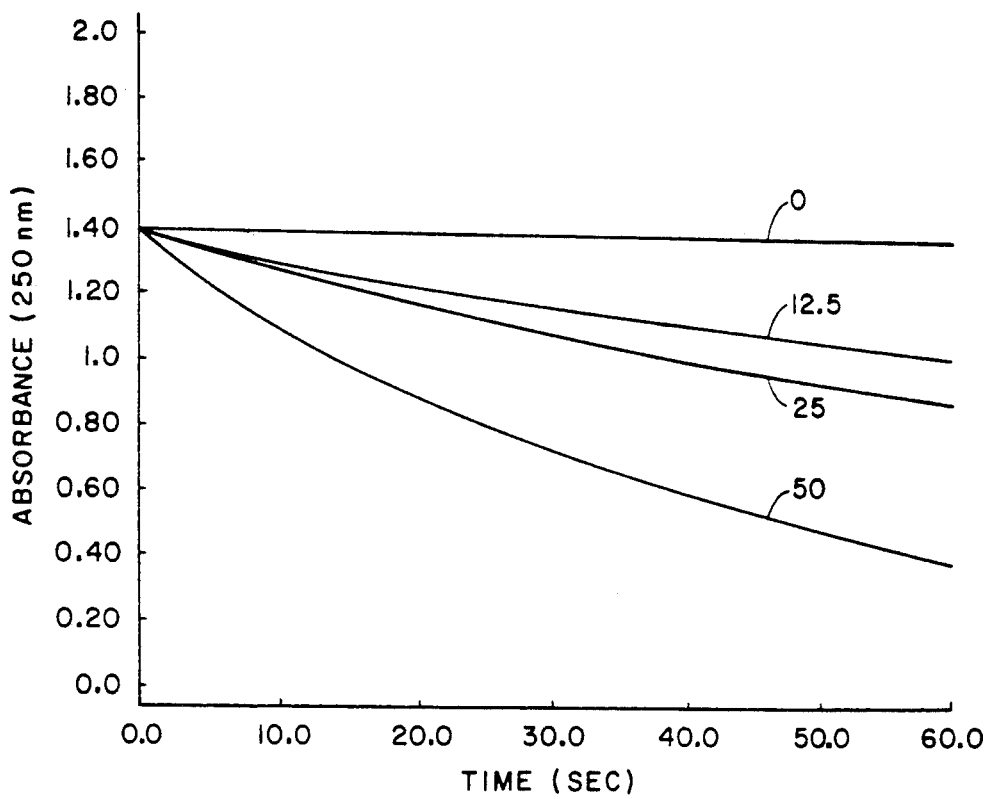
FIG. 3 is a series of plots of $A_{265}$ vs. time illustrating the rate of ascorbic acid oxidation by 0.5 mM potassium bromate and Fe(III)-HEDTA over the concentration range of 0 $\mu$M to 50 $\mu$M Fe(III)-HEDTA at pH 6.5.

In particular, FIG. 1 includes a series of plots of absorbance at 265 nm (A$_{265}$) vs. time for solutions at pH 6.5 that were 0.1 mM in ascorbic acid, 25 μM in Fe(III)-HEDTA, and were either 0, 0.5, 1, 5 or 10 mM in potassium bromate. A decrease in A$_{265}$ shows that ascorbic acid is oxidized. Therefore, FIG. 1 shows that in the absence of potassium bromate (0 mM KBrO$_3$), the A$_{265}$ slowly, but measurably, decreases due to the presence of the Fe(III)-HEDTA. As the concentration of potassium bromate increased over the range of 0.5 mM to 10 mM the rate of change in A$_{265}$ increases. FIG. 2 shows that plotting the first order rate constant (k, sec$^{-1}$) for the oxidation step vs. the potassium bromate concentration provided a straight line that intersects the y-axis at 0.01 sec$^{-1}$. Because the rate constant for the reaction is proportional to the potassium bromate concentration under these conditions, the reoxidation of Fe(II) to Fe(III) apparently is the slow step in this ascorbate oxidation mechanism. FIG. 3 shows that when the potassium bromate level was fixed at 0.5 mM and the Fe(III)-HEDTA concentration was increased over the range of 0 to 50 μM, the rate of ascorbic acid oxidation was a function of the Fe(III)-HEDTA concentration. Accordingly, as the Fe(III)-HEDTA concentration is increased, the rate of ascorbic acid oxidation is increased.

Therefore, and in accordance with an important feature of the present invention, bromate ion, chlorate ion or perchlorate ion, chromate ion, an organic oxidant like a peroxide, a hydroperoxide or a N-halo compound, is included in the indicator reagent composition of the present invention as a cooxidant to complete the oxidation-reduction cycle of the metal ion in the metal ion complex. The metal ion complex, like a ferric ion chelate, catalytically oxidizes the ascorbate, and the ferric ion then is regenerated by the cooxidant. Accordingly, the cooxidant increases the sensitivity of an assay for a predetermined analyte. The improved indicator reagent composition also demonstrates the advantages of low toxicity, stability, a minimum of side reactions and compatibility between ingredients of the indicator reagent composition. As will be demonstrated more fully hereinafter, it is both surprising and unexpected for an indicator reagent composition, including bromate ion, chlorate ion or perchlorate ion, chromate ion, an organic oxidant like a peroxide, a hydroperoxide or a N-halo compound, to eliminate the secondary interfering affects of the reduced metal ion of the metal ion complex at the essentially neutral pH wherein a test sample is assayed for a predetermined analyte.

In addition to the essential ingredients described above, the indicator reagent composition can include a sufficient amount of a suitable buffer, such that the indicator dye changes color as a result of an interaction between the predetermined analyte and the redox mediator, and not as a result of a change in pH. Test samples often have a pH outside the desired pH range for the assay of interest and therefore a buffer is added to the test composition. Accordingly, it has been demonstrated that any of various known types of buffers can be included in the indicator reagent composition of the present invention. The buffer is especially important in a commercially-acceptable dry phase test strip that resists the affects of urine pH and urine specific gravity. The function of the buffer is to maintain the indicator reagent composition at a proper pH to stabilize the indicator reagent composition and produce the desired color transition in the indicator dye during the assay.

A buffer is included in the indicator reagent composition of the present invention usually in a concentration range of between 0 mM to about 600 mM, and preferably between about 50 mM to about 400 mM, although in particular situations the concentration of the buffer can be above or below this range. To achieve the full advantage of the present invention, the optional buffer is present in a concentration ranging from about 150 mM to about 300 mM. It has been found that for optimum assay results, the pH of the indicator reagent composition generally should be maintained at a slightly acidic to a neutral pH value. Therefore, a pH of from about 5 to about 7, and preferably of from about 6 to about 7, provides a more spectacular and a more easily differentiable color transition in the assay for a predetermined analyte. Surprisingly, it has been found that bromate ion, chlorate ion, perchlorate ion, chromate ion, an organic oxidant like a peroxide, a hydroperoxide or a N-halo compound, effectively oxidizes the reduced metal ion at this slightly acidic to neutral pH range such that the full color transition is detected to provide optimum assay results, absent primary and secondary interferences attributed to ascorbate and to the reduced form of the metal ion respectively.

For example, the prior art teaches that when a ferric ion complex, like the ferric ion chelate of N-(2-hydroxyethyl)ethylenediaminetriacetic acid (Fe(III)-HEDTA), is included in the indicator reagent composition to provide the desired ascorbate resistance, the indicator reagent composition is buffered above a pH of 6.5, such as at a pH range of 6.7 to 7.0. Most preferably, the pH is buffered at 6.8 to 6.9. This pH range provides the best balance of sensitivity, stability and ascorbate resistance when assaying urine samples exhibiting highly variable pH values and specific gravity. Surprisingly, bromate ion, chlorate ion, perchlorate ion, chromate ion, an organic oxidant like a peroxide, a hydroperoxide or a N-halo compound, or a combination thereof, sufficiently oxidized the ferrous ion resulting from the ascorbate oxidation to ferric ion at this essentially neutral pH.

Therefore, optionally, well-known buffers such as acetate, phthalate; borate; trichloracetate; sulfosalicylate; phosphate; tartarate; citrate; succinate; maleic acid; 2,2-bis(hydroxymethyl)-2,2'2"-nitrilotriethanol; 3,3-dimethylglutaric acid; 3-N-morpholinopropanesulfonic acid (MOPS); malonic acid; 1,3-bis[tris(hydroxymethyl)methylamino]propane (Bis-tris); tris(hydroxymethyl)aminomethane (Tris); tris(hydroxymethyl)aminomethane-maleic acid (Tris-maleate); tris(hydroxymethyl)aminomethane-malonic acid (Tris-malonate); 3-N-(trishydroxymethyl)methylamino-2-hydroxypropanesulfonic acid (TAPSO); 2-([tris(hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N'-2-ethanesulfonic acid (HEPES); and other suitable buffers as are well known in the art, or combinations thereof, can be included as the optional buffer in the indicator reagent composition of the present invention.

The indicator reagent composition of the present invention, including an indicator dye, a redox mediator, a metal ion complex and a cooxidant selected from the group consisting of bromate ion, chlorate ion, perchlorate ion, chromate ion, an organic oxidant like a peroxide, a hydroperoxide or a N-halo compound, and combinations thereof, is utilized in an improved method to determine the presence or the concentration of a predetermined analyte in a liquid test sample. It has been demonstrated that the indicator reagent composition is stable previous to contact with a liquid test sample, and then interacts with a predetermined analyte in the test sample to produce a differentiable and measurable color transition, either visually or by instrument. Furthermore, in addition to the essential ingredients described above, the indicator reagent composition of the present invention can include a sufficient amount of optional ingredients, like a buffer, such that the indicator dye changes color upon contact and interaction with the oxygen that is catalytically released in the interaction between the predetermined analyte and the redox mediator. Accordingly, the color change, free from interfering affects attributed to ascorbate and to the reduced form of the metal ion, accurately establishes the presence or concentration of the predetermined analyte in the test sample.

In addition to the essential ingredients, the indicator reagent composition also can include other optional ingredients, in addition to the buffer, that do not materially alter the nature and the function of the essential ingredients, and that do not interfere with the assay for a predetermined analyte. For example, the indicator reagent composition optionally can include a compound to improve the wetting of the test pad of the test device by the test sample and to stabilize the oxidized indicator dye. This compound usually is an anionic surfactant or a nonionic surfactant. An anionic surfactant, such as a long carbon chain sulfate or sulfonate, like sodium dodecyl sulfate, dioctyl sodium sulfosuccinate and sodium dodecylbenzene sulphonate, is the preferred surfactant. Nonionic surfactants, such as an octoxynol, a nonoxynol or an ethoxylated fatty alcohol, also can be included in the indicator reagent composition of the present invention. The surfactant is included in the indicator reagent composition in a concentration of from 0 mM to about 200 mM, and preferably in a concentration of from about 50 mM to about 150 mM.

The indicator reagent composition also can include a polymeric material that improves the stability and uniformity of the color transition of the test device. Suitable polymeric materials include, but are not limited to, polyvinylpyrrolidone, polyvinyl alcohol, gum arabic, gelatin, algin, carrageenan, casein, albumin, methyl cellulose and similar natural and synthetic polymeric materials. The preferred polymeric material is a polyvinylpyrrolidone, such as PVP K-30, a polyvinylpyrrolidone of molecular weight 40,000 and available commercially from GAF Corp., New York, N.Y. The polymeric material generally is included in the indicator reagent composition in amounts from 0% to about 5%, and preferably from about 1% to about 4%, by total weight of the indicator reagent composition.

In addition, to improve the color resolution and differentiation of the color transition in a chromogenic assay for a predetermined analyte, inert background dyes can be included in the indicator reagent composition. Suitable background dyes include, but are not limited to, ethyl orange (4-(4-diethylaminophenylazo)-benzenesulfonic acid); Orange G (4-(2-hydroxy-(7,9 sodium disulfonate)-1-naphthylazo)benzene); disperse orange 11, 13 or 25; calcomine orange; methyl orange; and orange (II)(4-(2-hydroxy-1-naphthylazo)benzenesulfonic acid); or combinations thereof. A background dye is included in the indicator reagent composition of the present invention in a concentration ranging from 0 mM to about 2 mM, and preferably ranging from about 0.1 mM to about 1.2 mM.

The carrier vehicle for the ingredients included in the indicator reagent composition includes water. However, because of the limited water solubility of particular ingredients included in the indicator reagent composition, organic solvents such as methanol, ethanol, isopropyl alcohol, acetone, dimethylformamide, 1-methoxy-2-propanol, dimethylsulfoxide, acetonitrile, ethyl acetate and similar solvents can be included in the carrier vehicle. The selection of a suitable organic solvent or solvents, in addition to water, to include in the carrier vehicle of the indicator reagent composition is within the capability of those skilled in the art of designing diagnostic assays.

The amount of organic solvent present in the indicator reagent composition generally is in the range of from 0% to about 90%, and preferably from about 10% to about 70%, by weight of the carrier vehicle. A carrier vehicle comprising water and an organic solvent, like ethanol or acetonitrile, is especially preferred because a carrier matrix impregnated with the indicator reagent composition can be dried within a few to several minutes.

As previously described, the indicator reagent composition undergoes a color transition upon contact with a test sample to demonstrate the presence of a predetermined analyte. Furthermore, the intensity and degree of the color transition are used to determine the quantitative concentration of a predetermined analyte in the test sample by comparing or correlating the color produced by the test sample to colors produced by solutions having a known concentration of the predetermined analyte. In accordance with an important feature of the present invention, it has been demonstrated that an indicator reagent composition of the present invention provides a sufficiently resolved and differentiated color transition such that the amount of a predetermined analyte in a test sample can be measured and accurately determined without the use of color-measuring instruments, such as spectrophotometers or colorimeters. However, if desired, such color-measuring instruments can be used to measure the difference in color degree and intensity between the test sample and a solution having a known concentration of the predetermined analyte.

Accordingly, an assay for a predetermined analyte that utilizes an indicator reagent composition of the present invention improves the accuracy and reliability of the assay and also increases physician confidence in the assay. Additionally, because of the number of assays for a predetermined analyte being performed at home by the untrained patient, as opposed to trained physicians or technicians in the laboratory, it is imperative to provide accurate and reliable quantitative assay methods for a predetermined analyte, like glucose, in a test sample, like urine.

To demonstrate the new and unexpected results achieved by the method of the present invention, an indicator reagent composition, including an indicator dye, a redox mediator, a metal ion complex and a cooxidant selected from the group consisting of bromate ion, chlorate ion, perchlorate ion, chromate ion, an organic oxidant like a peroxide, a hydroperoxide or a N-halo compound, and combinations thereof, was used in dry phase test strip assay for a predetermined analyte. The dry phase test strip assay utilizing the indicator reagent composition of the present invention is performed in accordance with methods well known in the art. In general, the assay for a predetermined analyte is performed by contacting the whole blood, blood serum, blood plasma, urine or other test sample with an analyte detection device that includes the indicator reagent composition. The analyte detection device can be dipped into the test sample, or the test sample can be applied to the analyte detection device dropwise. The resulting change in color of the analyte detection device demonstrates the presence of the predetermined analyte; and, if so designed, the resulting color transition can be compared to a standardized color chart to provide a quantitative measurement of the concentration of the predetermined analyte in the test sample.

Typically, the analyte detection device is a reagent impregnated test strip, designed either as a single pad test strip (to assay only for a single analyte) or as a multiple pad test strip (to assay for several analytes simultaneously). For either type of reagent impregnated test strip, the test strip typically includes a support strip, or handle, normally constructed from a hydrophobic plastic, and a reagent test pad, comprising a bibulous or a nonbibulous carrier matrix incorporating the indicator reagent composition. In general, the carrier matrix is an absorbent material that allows the test sample to move, in response to capillary forces, through the carrier matrix to contact the indicator reagent composition and produce a detectable or measurable color transition.

The carrier matrix can be any substance capable of incorporating the chemical reagents required to perform the assay of interest, as long as the carrier matrix is substantially inert with respect to the chemical reagents, and is porous or absorbent relative to the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulosic beads, and especially fiber-containing papers such as filter paper or chromatographic paper; synthetic or modified naturally-occuring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. The carrier matrix is most advantageously constructed from bibulous filter paper or nonbibulous polymeric films. However, in every instance, the carrier matrix includes a hydrophilic or absorptive material. The handle usually is formed from a hydrophobic material such as cellulose acetate, polyethylene terephthalate, polycarbonate or polystyrene.

If the test strip is designed to assay for a predetermined analyte in a test sample, the carrier matrix can be any bibulous or nonbibulous material that allows permeation by the test sample to saturate the test pad of the test strip that incorporates the indicator reagent composition. To achieve the full advantage of the present invention, in the assay for a predetermined analyte in a test sample, the carrier matrix is a hydrophilic, bibulous matrix, including cellulosic materials, such as paper, and preferably filter paper. Filter paper possesses all of the qualities required of a bibulous matrix of the present invention, plus the advantages of abundant supply, favorable economics, and a variety of suitable grades. Filter paper has been found to be extremely satisfactory for use as a matrix material for suspending and positioning both the essential ingredients and any optional ingredients included in the indicator reagent composition.

To achieve the full advantage of the present invention, the indicator reagent composition is incorporated into a suitable carrier matrix and utilized in a dry phase test strip for the assay of a predetermined analyte in a test sample. The method of the present invention affords an economical, accurate and reliable assay, performable at home or in the laboratory, for the presence or concentration of a predetermined analyte in a test sample. In addition, the method of the present invention allows the detection, differentiation and measurement of a low concentration of a predetermined analyte in the test sample therefore making the assay more useful clinically.

In accordance with the method of the present invention, to perform a dry phase test strip assay for a predetermined analyte capable of interacting with an oxidase enzyme, like glucose, an aqueous solution, including from about 50 units to about 1000 units of the appropriate oxidase enzyme; from about 50 units to about 1000 units of a peroxidase enzyme; from about 5 mM to about 60 mM of an indicator dye; from 0.5 mM to about 50 mM of a metal ion complex; from about 5 mM to about 100 mM of a cooxidant selected from the group consisting of bromate ion, chlorate ion, perchlorate ion, chromate ion, an organic oxidant like a peroxide, a hydroperoxide or a N-halo compound, and combinations thereof; 0 mM to about 600 mM of a buffer such as a citrate buffer; from 0 mM to about 200 mM of a surfactant; from 0% to about 5% of a polymeric material; and any other desired optional ingredients, like background dyes or solvents, first is prepared. This aqueous solution then is adjusted to a pH of from about 5 to about 7 with a suitable organic acid or mineral acid, such as 1N hydrochloric acid. A bibulous matrix, such as filter paper, then is saturated with the aqueous solution by immersing or by spraying the aqueous solution onto sheets or precut strips of the filter paper.

Then, the aqueous solvent is removed by drying the saturated filter paper in an air oven at a temperature of from about 40° C. to about 100° C. for about 20 minutes. After oven drying, the reagent-impregnated filter paper is cut to an appropriate size, such as a pad having dimensions from about 0.25 cm by about 0.5 cm to about 0.5 cm by about 1.0 cm.

Similarly, to perform a dry phase test strip assay for a predetermined analyte that exhibits peroxidase activity, like occult blood, the redox mediator is changed from an oxidase enzyme and peroxidase to a hydroperoxide. Therefore, an aqueous solution, including from about 5 mM to about 60 mM of an indicator dye; from about 0.5 mM to about 50 mM of a metal ion complex; from about 5 mM to about 100 mM of a hydroperoxide; from about 5 mM to about 100 mM of a cooxidant; 0 mM to about 600 mM of a buffer such as sodium citrate; from 0% to about 5% of a polymeric material; from 0 mM to about 200 mM of a surfactant; and any other desired optional ingredients, like background dyes or solvents, first is prepared. Then, after the pH is adjusted to within the range of about 5 to about 7, the aqueous solution is incorporated into a carrier matrix, and the carrier matrix is dried and finally cut to an appropriate size as discussed above.

In either case, the dried and cut, reagent-impregnated filter paper then is secured to an opaque or transparent hydrophobic plastic handle with double-sided adhesive tape. The resulting test strip then is dipped into a test sample, such as a fresh, uncentrifuged urine sample, for a sufficient time to saturate the test pad with the sample. After waiting a predetermined time, such as from about 15 secs. to about 60 secs., the test strip is examined, either visually or by instrument, for a response. The color transition, if any, of the test pad reveals the presence or concentration of a predetermined analyte in the urine sample.

It should be understood that it is well within the experimental techniques of those skilled in the art of preparing test devices to determine the proper balance between size of reagent pad, the strength of reagent impregnating solutions, the amount of test sample, and the method of introducing the test sample to the test strip, such as by pipetting rather than dipping, in order to design a quantitative assay for a predetermined analyte utilizing the method and composition the present invention.

In many cases, simple visual observation of the test strip provides the desired information. If more accurate information is required, a color chart bearing color spots corresponding to various known concentrations of the predetermined analyte can be prepared for the particular indicator reagent composition used in the test strip. The resulting color of the test strip after contact with the test sample then can be compared with the color spots on the chart to determine the concentration of predetermined analyte in the test sample. If a still more accurate determination is required, a spectrophotometer or colorimeter can be used to more precisely determine the degree of color transition. In addition, the dry phase test strip assay can be made quantitative by employing spectrophotometric or colorimetric techniques, as opposed to visual techniques, in order to more reliably and more accurately measure the degree of color transition, and therefore more accurately measure the concentration of the predetermined analyte in the test sample, especially at lower concentrations, such as below one mg/dL.

Therefore, in accordance with an important feature of the present invention, it has been demonstrated that by incorporating an indicator reagent composition of the present invention into a suitable carrier matrix, the presence or concentration of a predetermined analyte in a test sample can be achieved by using a dry phase test strip. As previously discussed, a dry phase test strip used for the assay of a predetermined analyte in a test sample generally includes a carrier matrix comprising any absorbent matrix that is amenable to treatment with and incorporation of the indicator reagent composition; that permits the blood, urine or other test sample to permeate the carrier matrix rapidly enough to obtain a reliable assay relatively quickly; and that does not contaminate the blood, urine or other test sample either by test sample extraction of components comprising the carrier matrix or by appreciably altering the test sample in a way to make the subsequent assay inconclusive, inaccurate and doubtful.

In accordance with one embodiment of the present invention, the following dry phase test strips were prepared to perform a dry phase assay for a glucose. Glucose is capable of interacting with glucose oxidase to generate hydrogen peroxide. Therefore the following aqueous composition of Example I was prepared. Then, the composition of Example I was applied to a strip or sheet of a carrier matrix, like a film of porous polyurethane, with a Meyer rod.

EXAMPLES

Indicator Reagent Composition

| Ingredient | Example I Concentration | Example II Concentration |
|---|---|---|
| Tetramethylbenzidine (TMB) (Indicator Dye) | 35 mM | 35 mM |
| Sodium Citrate (Buffer) | 250 mM | 250 mM |
| Ferric chloride (Metal ion) | 5 mM | — |
| N-(2-hydroxyethyl)ethylenediaminetetraacetic acid | 5 mM | — |

| Ingredient | Example I Concentration | Example II Concentration |
|---|---|---|
| (Complexing agent for the metal ion) | | |
| Peroxidase | 1000 units/mL | 1000 units/mL |
| Potassium bromate | 20 mM | — |
| Glucose Oxidase | 1000 units/mL | 1000 units/mL |
| Sodium Dodecyl Sulfate (Surfactant) | 28 mM | 28 mM |
| Hydrochloric Acid (1 N) | to adjust pH to about 6.0 | to adjust pH to about 6.0 |

The layer of indicator reagent composition on the polyurethane matrix then was dried in an oven having a temperature ranging from about 45° C. to about 60° C. for about 10 minutes. The polyurethane matrix incorporating the dried indicator reagent composition then was cut into a pad having dimensions of about 0.5 cm by about 0.5 cm to provide a test pad comprising a carrier matrix incorporating an indicator reagent composition of the present invention. The test pad then was secured to a hydrophobic plastic handle with double-sided adhesive to provide a dry phase test strip of the present invention.

In addition, it should be understood that the indicator dye can be incorporated directly into the polyurethane matrix during the manufacture of the polyurethane matrix. Often the indicator dye has a low water solubility thereby making it difficult to solubilize the indicator dye in the aqueous solution. However, because the indicator dye often demonstrates excellent solubility in organic solvents, the indicator dye is solubilized in the organic solvent used in the manufacture of the polyurethane matrix.

To demonstrate the new and unexpected results achieved by the method of the present invention, dry phase test strips incorporating an indicator reagent composition of the present invention (Example I) were compared to dry phase test strips incorporating an indicator reagent composition (Example II) including the ingredients of Example I, except the bromate ion, the ferric chloride and the N-(2-hydroxyethyl)ethylenediaminetetraacetic acid were omitted. The test strips incorporating the composition of Example II were used as a control to demonstrate the improved assays provided by an indicator reagent composition of the present invention, i.e., Example I.

Individual dry phase test strips incorporating either the composition of Example I or the composition of Example II were compared in the assay of standardized solutions including 100 mg/dL glucose and from 0 mg/dL to 200 mg/dL ascorbic acid. The test strips were dipped into a standardized solution including the glucose and ascorbic acid, then approximately one minute after contacting the standardized solution, the reflectance of the test pad of the test strip was measured at 660 nm (nanometers) on an Advanced Research Rapid Scanner reflectance spectrometer, of the Diagnostics Division of Miles Inc., Elkhart, Ind. The reflectance measurement represents the reactivity of a particular dry phase test strip towards a solution including a standardized amount of glucose.

TABLE II summarizes the reactivity of dry phase test strips including an indicator reagent composition absent bromate ion and metal ion complex (Example II), and test strips including a composition of the present invention (Example I). In general, from TABLE II, assays performed with test strips incorporating an indicator reagent composition of Example I show a substantially greater resistance to ascorbic acid interference than assays performed with test strips incorporating the composition of Example II.

TABLE II

Improved Ascorbate Resistance of Test Strips Including a Metal Ion Complex and Bromate Ion

| Test Sample | Glucose Concentration (mg/dL) | Ascorbate Concentration (mg/dL) |
|---|---|---|
| A | 100 | 0 |
| B | 100 | 50 |
| C | 100 | 100 |
| D | 100 | 200 |

| Test Sample | Indicator Reagent Composition | |
|---|---|---|
| | EX. 1 | EX. 2 |
| A | 100[1] | 100[1] |
| B | >30 | 30 |
| C | >30 | 0 |
| D | >30 | 0 |

[1] Apparent glucose concentration in the standardized test sample, in mg/dL.

The test strips incorporating an indicator reagent composition of the present invention (Example I) were evaluated for ascorbate resistance by comparison to control strips incorporating the indicator reagent composition of Example II. In each assay, the strip was dipped into standardized glucose solution including 0, 30 or 100 mg/dL of glucose, or including 100 mg/dL glucose and either 0, 50, 100 or 200 mg/dL of ascorbic acid. The standardized solutions including 0, 30 or 100 mg/dL glucose, and no ascorbic acid, provided standardized responses to glucose. The responses of assays performed on solutions include 100 mg/dL glucose and varying amounts of ascorbic acid were compared to these standardized responses.

In general, the data presented in TABLE II show that a test strip incorporating a composition of the present invention (Example I) demonstrate a detectable color transition with an apparent glucose concentration of greater than 30 mg/dL, even in the presence of 200 mg/dL ascorbic acid. However, a test strip including a composition absent a metal ion complex and bromate ion (Example II) shows an apparent glucose concentration of 0 mg/dL in the presence of 100 mg/dL ascorbic acid.

In particular, a test sample including no ascorbate as an interferent (Test Sample A) is accurately assayed for glucose (100 mg/dL) by the composition of Example I or the composition of Example II. However, when ascorbate is included in the test sample, the composition of Example I demonstrated a sufficient response to show that greater than 30 mg/dL of glucose is present in the test sample regardless of the amount of interfering ascorbate that is present. However, for test strips incorporating the composition of Example II, if 100 mg/dL or 200 mg/dL of ascorbic acid is included in the test sample (Test Samples C and D), the test strip did not undergo a color transition. In contrast, a test strip incorporating a composition of the present invention, still demonstrated a response of greater than 30 mg/dL glucose when 200 mg/dL ascorbic acid was present in the test sample (Test Sample D). A composition of the present invention similarly provided improved assay results when 50 mg/dL ascorbic acid is present in the test sample.

To further demonstrate the usefulness of the present invention, it has been found that bromate ion and Fe(III)-HEDTA also effectively eliminate ascorbate interference in an assay for cholesterol. TABLE III summarizes the results of five wet phase cholesterol assays. The assays were performed to determine the effectiveness of a composition including cholesterol oxidase, peroxidase, tetramethylbenzidine (TMB) dye, a metal ion complex and a cooxidant in reducing or eliminating interferences due to ascorbic acid in an assay for cholesterol.

TABLE III

Improved Ascorbate Resistance in the Assay for Cholesterol

| Test Sample | Water[1] | Buffer[2] | Cholesterol Oxidase[3] | Peroxidase[4] | TMB[5] |
|---|---|---|---|---|---|
| A | 0.86 | 0.10 | 10 | 10 | 10 |
| B | 0.85 | 0.10 | 10 | 10 | 10 |
| C | 0.84 | 0.10 | 10 | 10 | 10 |
| D | 0.83 | 0.10 | 10 | 10 | 10 |
| E | 0.82 | 0.10 | 10 | 10 | 10 |

| Test Sample | Ascorbic Acid[6] | Fe(III)-HEDTA[7] | $KBrO_3$[8] | Cholesterol[9] | Color[10] Formation |
|---|---|---|---|---|---|
| A | — | — | — | 10 | Yes |
| B | 10 | — | — | 10 | No |
| C | 10 | 10 | — | 10 | No |
| D | 10 | 10 | 10 | 10 | No |
| E | 10 | 10 | 20 | 10 | Yes |

[1] in milliliters (mL), each test sample had a total volume of 1 mL;
[2] in mL, the buffer is 1M 2-(N-morpholino)ethanesulfonic acid (MES), pH-6.5.
[3] in microliters (μL), of 100 mg/mL of cholesterol oxidase in water (1330 units/mL), available from GDS Technology, Inc., Elkhart, IN.;
[4] in μL, of 100 mg/mL of peroxidase in water (103 units/mg);
[5] in μL, of a 100 mM solution of tetramethylbenzidine (TMB) in 1-methoxy-2-propanol, as the indicator dye;
[6] in μL, of a 0.56M solution of ascorbic acid (10% ascorbic acid by weight), test samples B through E each include 5.6 mM (millimolar) ascorbic acid;
[7] in μL, of a 100 mM solution of Fe-HEDTA, test sample C through E each include 1.0 mM Fe(III)-HEDTA;
[8] in μL, of a 0.2M aqueous solution of potassium bromate, test sample D includes 2.0 mM $KBrO_3$ and test sample E includes 4.0 mM $KBrO_3$;
[9] in μL, of a serum including 333 mg/dL (milligram/deciliter) cholesterol; and
[10] test sample was examined for the formation of a blue color The tests illustrated in TABLE III were performed in a 12 mm (millimeter) by 75 mm glass test tube. For test sample A, the cholesterol oxidase, the peroxidase, the TMB and the MES buffer solutions first were added to the test tube. Then, the reaction was initiated by adding the cholesterol-containing serum to the test tube. The total volume in the test tube for test sample A, and for test samples B through E, was 1.00 mL. After about from 10 to 15 seconds, the reaction solution became blue in color, indicating the presence of cholesterol in the test sample. Test sample A was the control sample that included no ascorbic acid as an interferent, and accordingly the indicator dye underwent a full color transition in response to the amount of cholesterol present in test sample A.

Test sample B was subjected to an identical assay, except that test sample B also was 5.6 mM in ascorbic acid. The ascorbic acid interfered sufficiently such that no color transition of the reaction solution to blue was observed. Test sample C was subjected to an identical assay as test sample B except that test sample C also was 1.0 mM in Fe(III)-HEDTA. Again no color transition to blue was observed. Although the Fe(III)-HEDTA eliminated the ascorbate interference, the generation of ferrous ions from the Fe(III)-HEDTA/ascorbate interaction provided a secondary interference in that the ferrous ions interacted with the oxidized, colored form of TMB to regenerate ferric ions and the reduced, colorless form of TMB. Accordingly, the assay was a false negative assay for cholesterol.

Test sample D was subjected to an identical assay as test sample C, except that test sample D also was 2 mM in potassium bromate. Again no color transition to blue was observed. However, in test sample E, identical to test sample D except for being 4 mM in potassium bromate, a color change to blue was observed. This color change was essentially identical in degree and intensity to the color change of test sample A, thereby showing that the interfering affects of the ascorbic acid have been overcome by including a metal ion complex and a sufficient amount of a suitable cooxidant in the indicator reagent composition.

To demonstrate that other metal complexes and other cooxidants also can be used in an indicator reagent composition of the present invention to reduce or eliminate the interfering affects of ascorbic acid in an assay for a predetermined analyte, several dry phase test strips including different metal ion complexes and different cooxidants were prepared and used to assay for glucose. The test strips utilized filter paper as the carrier matrix, and incorporated an indicator reagent composition comprising tetramethylbenzidine dye (TMB), glucose oxidase and peroxidase into the carrier matrix. The indicator reagent composition also included a buffer and either a cooxidant or a metal ion complex or a combination of a cooxidant and a metal ion complex. The test strips were used to assay samples that included glucose as the predetermined analyte and ascorbic acid as the interferent. The test strips then were visually compared to determine the degree and intensity of a color transition. The experimental results are illustrated in TABLE IV.

TABLE IV

Metal Complexes and Cooxidants to Eliminate Ascorbate Interferences

| Exp. No. | Buffer | Metal Complex | Cooxidant |
|---|---|---|---|
| 1 | MES[4] | 0 | 0 |
| 2 | MES | 0 | 0 |
| 3 | MES | Fe(III)-HEDTA[5] (5 mM) | 0 |
| 4 | MES | 0 | Bromate (20 mM) |
| 5 | MES | Fe(III)-HEDTA (5 mM) | Bromate (20 mM) |
| 6 | MES | Fe(III)-HEDTA (5 mM) | Bromate (20 mM) |
| 7 | MES | 0 | 0 |
| 8 | MES | Fe(III)-HEDTA (5 mM) | Bromate (20 mM) |
| 9 | MES | HAC[6] (5 mM) | Bromate (20 mM) |
| 10 | MES | CPD[7] (5 mM) | Bromate (20 mM) |
| 11 | MES | Pb(Ac)$_4$[8] (25 mM) | Bromate (25 mM) |
| 12 | MES | Hg$^{+2}$[9] (25 mM) | Bromate (25 mM) |
| 13 | MES | Hg$^{+2}$ (25 mM) and Fe(III)-HEDTA (5 mM) | 0 |
| 14 | MES | Hg$^{+2}$ (25 mM) | 0 |
| 15 | citrate[10] | Fe(III)-HEDTA (5 mM) | Chlorate (10 mM) |
| 16 | citrate | Fe(III)-HEDTA (5 mM) | Chlorate (20 mM) |
| 17 | citrate | Fe(III)-HEDTA (5 mM) | Chlorate (30 mM) |
| 18 | citrate | 0 | Chlorate (30 mM) |
| 19 | citrate | Fe(III)-HEDTA (5 mM) | Perchlorate (10 mM) |
| 20 | citrate | Fe(III)-HEDTA (5 mM) | Perchlorate (20 mM) |
| 21 | citrate | Fe(III)-HEDTA (5 mM) | Perchlorate (30 mM) |
| 22 | citrate | 0 | Perchlorate (30 mM) |
| 23 | citrate | Fe(III)-HEDTA (5 mM) | Iodate (10 mM) |
| 24 | citrate | Fe(III)-HEDTA (5 mM) | Iodate (20 mM) |
| 25 | citrate | Fe(III)-HEDTA (5 mM) | Iodate (30 mM) |
| 26 | citrate | 0 | Iodate (30 mM) |
| 27 | PO$_4$[11] | Gan-His-Cu[12] | Bromate (5 mM) |
| 28 | PO$_4$ | Gan-His-Cu | 0 |
| 29 | PO$_4$ | Fe(III)-HEDTA (5 mM) | Chromate (5 mM) |
| 30 | PO$_4$ | 0 | Chromate (5 mM) |
| 31 | PO$_4$ | Fe(III)-HEDTA (5 mM) | DBDH[13] (5 mM) |
| 32 | PO$_4$ | 0 | DBDH (5 mM) |

TABLE IV-continued

Metal Complexes and Cooxidants to Eliminate Ascorbate Interferences

| Exp. No. | Glucose[1] | Ascorbate[2] | Strip Reactivity[3] |
|---|---|---|---|
| 1 | 100 | 100 | − |
| 2 | 100 | 50 | + |
| 3 | 100 | 100 | − |
| 4 | 100 | 100 | − |
| 5 | 0 | 100 | − |
| 6 | 100 | 0 | ++++ |
| 7 | 100 | 0 | ++++ |
| 8 | 100 | 100 | ++++ |
| 9 | 100 | 100 | − |
| 10 | 100 | 50 | − |
| 11 | 100 | 50 | + |
| 12 | 100 | 50 | ++++ |
| 13 | 100 | 50 | +++ |
| 14 | 100 | 50 | +++ |
| 15 | 100 | 100 | ++ |
| 16 | 100 | 100 | ++ |
| 17 | 100 | 100 | ++ |
| 18 | 100 | 100 | − |
| 19 | 100 | 100 | ++ |
| 20 | 100 | 100 | ++ |
| 21 | 100 | 100 | ++ |
| 22 | 100 | 100 | − |
| 23 | 100 | 100 | ++++ |
| 24 | 100 | 100 | ++++ |
| 25 | 100 | 100 | ++++ |
| 26 | 100 | 100 | ++++ |
| 27 | 100 | 100 | +++ |
| 28 | 100 | 100 | − |
| 29 | 100 | 100 | ++++ |
| 30 | 100 | 100 | + |
| 31 | 100 | 100 | ++++ |
| 32 | 100 | 100 | + |

[1] Glucose concentration in the test sample, in mg/dL;
[2] Ascorbate concentration in the test sample, in mg/dL;
[3] ++++ means reactivity of the test strip is essentially equal to the reactivity observed when the strip is dipped into control sample containing no ascorbic acid, +++ means slightly less reactivity than ++++, ++ means less activity than +++, + means less activity than ++, and − means no activity;
[4] MES is 2-(N-morpholino)ethanesulfonic acid, present at 200 mM to provide a pH of 6.5;
[5] Solution of ferric ion complex with HEDTA;
[6] HAC is hexamminecobalt(III) chloride;
[7] CPD is cobalt(III) 2,4-pentanedionate;
[8] Pb(Ac)$_4$ is lead tetraacetate;
[9] Hg$^{+2}$ is a mercuric nitrate solution;
[10] citrate is citrate buffer, present at 400 mM to provide a pH of 6.5;
[11] PO$_4$ is phosphate buffer, present at 400 mM to provide a pH of 6.5;
[12] Gan-His-Cu is a GANTREZ-histamine-copper complex disclosed in U.S. Application Ser. No. 337,620; and
[13] DBDH is diisopropylbenzene dihydroperoxide.

TABLE IV shows the particular usefulness of Fe(III)-HEDTA as the metal complex and potassium bromate as the cooxidant in an indicator reagent composition of the present invention. Experiments 1 and 3 through 5 showed that the strip has no reactivity (no color change) in the presence of 100 mg/dL ascorbate if either one or both of the metal ion complex and the cooxidant is absent from the indicator reagent composition. However, Experiment 2 showed that the strip demonstrates a slight reactivity in the absence of a metal ion complex and a cooxidant when the ascorbate acid concentration in the test sample was decreased to 50 mg/dL. Experiment 7 was a control experiment showing the strip reactivity (maximum color change) towards glucose in the absence of ascorbate, cooxidant and metal ion complex. The color change demonstrated in Experiment 7 was the standard. The color changes of the test strips in the other experiments were compared to the standard color change of Experiment 7. Experiment 6 demonstrated that the metal ion complex and cooxidant do not adversely affect test strip reactivity when ascorbate is absent from the test sample. Experiment 8 showed that the metal ion complex and the cooxidant effectively overcame the interfering affects of ascorbic acid, and provided a strip activity essentially identical to the control Experiment 7.

Experiments 9 through 11 illustrated that cobalt ion complexes and lead ion complexes are not effective metal ion complexes in the indicator reagent composition of the present invention. This result is most easily demonstrated by comparing the reactivity of the test strips of Experiments 9 and 10 to the reactivities of the test strips of Experiments 8 and 2, wherein the HAC/bromate-containing test strip (Exp. 9) is unreactive, whereas the Fe(III)-HEDTA/bromate-containing test strip (Experiment 8) is fully reactive, and wherein the CPD/bromate-containing test strip (Experiment 10) is less reactive than a test strip absent a metal ion complex and a cooxidant (Experiment 2). Similarly, the lead ion complex and cooxidant included in the test strip of Experiment 11 did not increase the reactivity of the test strip over the reactivity of the test strip in Experiment 2 that was absent a metal ion complex and a cooxidant.

Experiments 12 through 14 showed that mercuric ion is an effective metal ion in the indicator reagent composition of the present invention to eliminate ascorbate interference. Experiment 14 illustrated that mercuric ion alone provides a relatively highly-reactive test strip in the presence of ascorbic acid. Including Fe(III)-HEDTA in the test strip with the mercuric ion (Experiment 13) did not increase the reactivity of the test strip appreciably, but including bromate ion as a cooxidant, with the mercuric ion, in the test strip improved the reactivity of the test strip to provide a maximum color transition (Experiment 12).

Experiments 15 through 18 demonstrated that chlorate ion is an effective cooxidant in the indicator reagent composition of the present invention. Experiment 3 showed that including Fe(III)-HEDTA in a test strip, without a cooxidant, provides a test strip having no reactivity in the presence of 100 mM ascorbic acid. Experiments 15 through 17 showed that test strips including Fe(III)-HEDTA and chlorate ion demonstrate an appreciably improved reactivity to test samples including ascorbic acid in comparison to the test strip of Experiment 3. Experiment 18 further showed that chlorate ion is a cooxidant, as opposed to a primary oxidant for ascorbic acid. In the absence of Fe(III)-HEDTA, the test strip of Experiment 18 exhibited no reactivity in the presence of 100 mM ascorbic acid. Therefore, the Fe(III)-HEDTA is present to eliminate the primary interference of the ascorbic acid, and the chlorate ion is present to reduce the secondary interfering affects of the ferrous ion.

Similarly, Experiments 19 through 22 demonstrated that perchlorate ion is an effective cooxidant in the indicator reagent composition of the present invention. Like the above-discussed experiments including chlorate ion, Experiments 19 through 21 showed that test strips including Fe(III)-HEDTA and perchlorate ion demonstrate a substantially improved reactivity to test samples including ascorbic acid in comparison to the test strip of Experiment 3. Experiment 22 illustrated that chlorate ion is a cooxidant, and not a primary oxidant of ascorbic acid. The perchlorate ion did not improve test strip reactivity in the absence of Fe(III)-HEDTA, and therefore the perchlorate ion reduces the secondary interfering affects of the oxidized form of the metal ion in the metal ion complex.

In contrast to the chlorate ion and the perchlorate, the iodate ion, as shown in Experiments 23 through 26, is a primary oxidant. Experiment 26 showed that iodate ion, alone, eliminated the interfering affects of ascorbate ion in a test sample, and therefore provided a test strip having a maximum reactivity. The presence of Fe(III)-HEDTA therefore is not necessary in the case where iodate ion is present.

Experiments 27 and 28 showed that bromate ion also is an effective cooxidant in an indicator reagent composition including a cupric ion complex. The particular cupric ion complex tested was disclosed in the previously-discussed U.S. patent application Ser. No. 337,620. However, it is envisioned that other cupric ion complexes also can be included with a cooxidant selected from the group consisting of bromate ion, chlorate ion, perchlorate ion, chromate ion, organic oxidants like a peroxide, a hydroperoxide or a N-halo compound, and combinations thereof in an indicator reagent composition of the present invention.

Experiments 29 and 30 showed that chromate ion also is an effective cooxidant in an indicator reagent composition including Fe(III)-HEDTA. Similarly, Experiments 31 and 32 showed that an organic oxidant, like the hydroperoxide DBDH, also is an effective cooxidant in an indicator reagent composition including Fe(III)-HEDTA.

Consequently, and in accordance with an important feature of the present invention, the continuing and substantial problem of ascorbic acid interference in dry phase test strip assays for a predetermined analyte is essentially eliminated, and a more sensitive assay, especially to low concentrations of a predetermined analyte, is provided. The indicator reagent composition of the present invention essentially eliminates the primary interfering affects of ascorbic acid by including a metal ion complex. The indicator reagent composition also essentially eliminates the secondary interfering affects attributed to the reduced form of the metal ion in the metal ion complex by including a cooxidant selected from the group consisting of bromate ion, chlorate ion, perchlorate ion, chromate ion, organic oxidants like a peroxide, a hydroperoxide or a N-halo compound, and combinations thereof. The essential elimination of the primary and secondary interfering affects of ascorbic acid is an unexpected improvement in the art of dry phase test strip assays for a predetermined analyte, such as the assay for occult blood, cholesterol or glucose, and similar analytes that are capable of either interacting with an oxidase enzyme or exhibiting peroxidase activity.

Consequently, and in accordance with an important feature of the present invention, more accurate and reliable assays for a predetermined analyte in urine, blood serum, blood plasma and other test samples can be performed by utilizing the indicator reagent composition of the present invention. In general, an indicator reagent composition of the present invention, including a metal ion complex and a cooxidant selected from the group consisting of bromate ion, chlorate ion, perchlorate ion, chromate ion, an organic oxidant like a peroxide, a hydroperoxide or a N-halo compound, and combinations thereof, demonstrates an improved ability to eliminate the primary interfering affects of ascorbic acid and the secondary interfering affects of the reduced form of the metal ion of the metal ion complex; undergoes a more spectacular color transition in response to the concentration of a predetermined analyte in a test sample; does not interfere with indicator dye oxidation by a predetermined analyte and the redox mediator; and does not interfere with ascorbate resistance provided by a metal ion complex.

Obviously, many modifications and variations of the present invention as hereinbefore set forth can be made without departing from the spirit and scope thereof and therefore only such limitations should be imposed as are indicated by the appended claims.

We claim:

1. A composition which exhibits a sufficient color transition upon contacting a test sample to demonstrate the presence or concentration of a predetermined analyte in the test sample, wherein the predetermined analyte interacts with an oxidase enzyme or exhibits peroxidase activity, comprising:
   (a) an indicator dye;
   (b) a redox mediator;
   (c) a metal ion complex which includes a metal ion selected from the group consisting of ferric ion, mercuric ion, stannic ion, nickel(II) ion, magnesium(III) ion, cadmium(II) ion, zinc(II) ion, molybdenum(V) ion, chromium(IV) ion, vanadium(III) ion, ceric(IV) ion and combinations thereof;
   (d) a cooxidant selected from the group consisting of bromate ion, chlorate ion, perchlorate ion, chromate ion, a peroxide, a N-halo compound and combinations thereof; and
   (e) a suitable carrier vehicle.

2. The composition of claim 1 wherein the indicator dye is present in an amount ranging from 5 millimoles to 60 millimoles per liter of the composition.

3. The composition of claim 1 wherein the indicator dye is a redox indicator.

4. The composition of claim 3 wherein the redox indicator is selected from the group consisting of: benzidine; o-tolidine; a 3,3',5,5'-tetraalkylbenzidine, wherein the alkyl group includes from one to about six carbon atoms; o-dianisidine; 2,7-diaminofluorene; bis(N-ethylquinol-2-one)-azine; (N-methylbenztriazol-2-one)-(1-ethyl-3-phenyl-5-methyltriazol-2-one)-azine; and combinations thereof.

5. The composition of claim 1 wherein the indicator dye is 3,3',5,5'-tetramethylbenzidine.

6. The composition of claim 1 wherein the predetermined analyte interacts with an oxidase enzyme and the redox mediator comprises an oxidase enzyme and a peroxidase.

7. The composition of claim 6 wherein the predetermined analyte is selected from the group consisting of glucose, alcohol, cholesterol, triglycerides and uric acid.

8. The composition of claim 6 wherein oxidase enzyme is present in an amount ranging from 50 units to 1000 units per milliliter of the composition.

9. The composition of claim 6 wherein oxidase enzyme is selected from the group consisting of glucose oxidase, cholesterol oxidase, uricase, aryl-alcohol oxidase, L-gluconolactone oxidase, galactose oxidase, pyranose oxidase, L-sorbase oxidase, pyridoxin 4-oxidase, alcohol oxidase, L-2-hydroxyacid oxidase, pyruvate oxidase, oxalate oxidase, glyoxylate oxidase, dihydroorotate oxidase, lathosterol oxidase, choline oxidase, glycolate oxidase, glycerol-3-phosphate oxidase, xanthine oxidase, sarcosine oxidase, N-methylamino-acid oxidase, $N^6$-methyl-lysine oxidase, 6-hydroxy-L-nicotine oxidase, 6-hydroxy-D-nicotine oxidase, nitroethane oxidase, sulphite oxidase, thiol oxidase, cytochrome c oxidase, Pseudomonas cytochrome oxidase, ascorbate oxidase, o-aminophenol oxidase, 3-hydroxyanthranilate oxidase and combinations thereof.

10. The composition of claim 6 wherein the peroxidase enzyme is present in an amount ranging from 50 units to 1000 units per milliliter of the composition.

11. The composition of claim 1 wherein the predetermined analyte exhibits peroxidase activity and the redox mediator comprises a hydroperoxide.

12. The composition of claim 11 wherein the predetermined analyte is selected from the group consisting of hemoglobin, a hemoglobin derivative, an erythrocyte, myoglobin and combinations thereof.

13. The composition of claim 11 wherein the hydroperoxide is present in an amount ranging from 5 millimoles to 100 millimoles per liter of the composition.

14. The composition of claim 11 wherein the hydroperoxide is an organic hydroperoxide.

15. The composition of claim 11 wherein the hydroperoxide is selected from the group consisting of cumene hydroperoxide, t-butyl hydroperoxide, diisopropylbenzene hydroperoxide, 1-hydroxycyclohexane-1-hydroperoxide, 2,5-dimethylhexane-2,5-dihydroperoxide, paramenthane hydroperoxide, 1,4-diisopropylbenzene monohydroperoxide, p-t-butylisopropylbenzene hydroperoxide, 2-(α-hydroperoxyisopropyl)-6-isopropylnaphthalene, tetralin hydroperoxide and combinations thereof.

16. The composition of claim 1 wherein the metal ion complex is present in an amount ranging from 0.5 millimole to 50 millimoles per liter of the composition.

17. The composition of claim 1 wherein the metal ion complex includes a complexing agent selected from the group consisting of a polycarboxyalkylamine, a polycarboxylic acid, a polycarboxylic acid salt, a polyhydroxy compound, a lignosulfonate, a glucoheptonate, bis(dimethylglyoximato), a salicylate derivative, a dithioate derivative, a polyethyleneamine, a 2,4-pentanedione derivative, a dipyridine derivative, triethylenepyridine amine, a polypeptide containing cysteine, glycine or histidine, a proline derivative, a thiocrown ether, a triphenylphosphine and combinations thereof.

18. The composition of claim 1 wherein the metal ion complex is a ferric ion complex.

19. The composition of claim 18 wherein the ferric ion complex is selected from the group consisting of ferric ion complexes of N-(2-hydroxyethyl)ethylenediaminetriacetic acid, ethylenediaminetetraacetic acid, cyclohexylenediaminetetraacetic acid, nitrilotriacetic acid, iminodiacetic acid, ethylenediaminediacetic dipropionic acid, hydroxyethyliminodiacetic acid, diethylenetriaminepentaacetic acid, ethylenebis(oxyethylenenitrilo)tetraacetic acid, N-(2-acetamido)iminodiacetic acid, citric acid, gluconic acid, a glucoheptonate, bissalicylaldeheethylenedimato, triethylenepyridine amine and combinations thereof.

20. The composition of claim 1 wherein the metal ion complex is the ferric ion complex of N-(2-hydroxyethyl)ethylenediaminetriacetic acid, ethylenediaminetetraacetic acid or a combination thereof.

21. The composition of claim 1 wherein the cooxidant is present in an amount ranging from 5 millimoles to 100 millimoles per liter of the composition.

22. The composition of claim 1 wherein the cooxidant is bromate ion, chlorate ion, perchlorate ion, chromate ion or a combination thereof, wherein the cooxidant is included in the composition as a water-soluble salt, the water-soluble salt having a cation selected from the group consisting of potassium, sodium, lithium, calcium, magnesium, ammonium, alkylammonium, hydroxyalkylammonium, alkylphosphonium and combinations thereof, wherein an alkyl or a hydroxyalkyl group includes from one to about six carbon atoms.

23. The composition of claim 1 wherein the cooxidant is bromate ion, chlorate ion, perchlorate ion, chromate ion or a combination thereof, wherein the cooxidant is included in the composition as a water-insoluble salt, the water-insoluble salt having a cation selected from the group consisting of quaternary alkylammonium, cyanine, pyridinium, picolinium, quinalkinium, quinolinium, quaternary alkyl phosphonium and combinations thereof, wherein an alkyl group includes at least six carbon atoms.

24. The composition of claim 1 wherein the cooxidant is a peroxide or a hydroperoxide selected from the group consisting of diisopropylbenzene hydroperoxide, diisopropylbenzene monohydroperoxide, phenylcyclohexane hydroperoxide, p-($\alpha$-hydroperoxyisopropyl)benzoic acid, p-(bromoisopropyl)benzene hydroperoxide, p-($\alpha$-hydroxy-$\alpha'$-hydroperoxyisopropyl)-benzene and combinations thereof.

25. The composition of claim 1 wherein the cooxidant comprises a 1-halobenzotriazole as the N-halo compound.

26. The composition of claim 1 wherein the suitable carrier vehicle comprises water.

27. The composition of claim 26 wherein the suitable carrier vehicle further comprises from 0% to 90% by weight of the carrier vehicle, of an organic solvent.

28. The composition of claim 1 having a pH in the range of from 5 to 7.

29. The composition of claim 1 further comprising a buffer.

30. The composition of claim 1 comprising from 20 millimole to 40 millimoles of the indicator dye 3,3',5,5'-tetramethylbenzidine per liter of the composition; a redox mediator comprising from 50 units to 250 units per milliliter of the composition of the oxidase enzyme glucose oxidase and from 50 units to 250 units per milliliter of the composition of peroxidase; from 1 millimole to 25 millimoles of the metal ion complex ferric N-(2-hydroxyethyl)ethylenediaminetriacetic acid per liter of the composition; and from 20 millimoles to 70 millimoles of bromate ion per liter of the composition, said composition exhibiting a sufficient color transition to demonstrate the presence or concentration of the predetermined analyte glucose in the test sample.

31. The composition of claim 30 further comprising a buffer and having a pH in the range of from 6 to 7.

32. The composition of claim 1 comprising from 20 millimoles to 40 millimoles of the indicator dye 3,3',5,5'-tetramethylbenzidine per liter of the composition; a redox mediator comprising from 25 millimoles to 75 millimoles of the hydroperoxide 1,4-diisopropylbenzene monohydroperoxide per liter of the composition; from about 1 millimole to 25 millimoles of the metal ion complex ferric N-(2-hydroxyethyl)-ethylenediaminetriacetic acid per liter of the composition; and from 20 millimoles to 70 millimoles of bromate ion per liter of the composition, said composition exhibiting a sufficient color transition to demonstrate the presence or concentration of the predetermined analyte hemoglobin.

33. The composition of claim 32 further comprising a buffer and having a pH in the range of from 6 to 7.

34. A composition exhibiting a sufficient color transition upon contacting a test sample to demonstrate the presence or concentration of a predetermined analyte in the test sample, wherein the predetermined analyte interacts with an oxidase enzyme or exhibits peroxidase activity, comprising:
   (a) an indicator dye;
   (b) a redox mediator;
   (c) mercuric nitrate;
   (d) a cooxidant selected from the group consisting of bromate ion, chlorate ion, perchlorate ion, chromate ion, a peroxide, a hydroperoxide, a N-halo compound and combinations thereof; and
   (e) a suitable carrier vehicle.

35. A method of determining the presence or concentration of a predetermined analyte in a test sample, wherein the predetermined analyte interacts with an oxidase enzyme or exhibits peroxidase activity, comprising:
   (a) contacting the test sample with a composition comprising an indicator dye; a redox mediator; a metal ion complex which includes a metal ion selected from the group consisting of a ferric ion, mercuric ion, stannic ion, nickel(II) ion, magnesium(III), cadmium(II) ion, zinc(II) ion, molybdenum(V) ion, chromium(IV) ion, vanadium(III) ion, ceric(IV) ion and combinations thereof; a cooxidant selected from the group consisting of bromate ion, chlorate ion, perchlorate ion, chromate ion, a peroxide, a N-halo compound and combinations thereof; and a suitable carrier vehicle, and
   (b) determining the presence or concentration of the predetermined analyte in the test sample from the intensity and degree of a color change of the composition.

36. The method of claim 35 wherein the intensity and degree of color change is determined visually or instrumentally.

37. The method of claim 35 wherein the presence or concentration of the predetermined analyte is determined by a dry phase assay.

38. The method of claim 35 wherein the test sample is a biological fluid.

39. The method of claim 38 wherein the biological fluid is urine, blood serum, blood plasma, gastrointestinal fluid, feces or vomit.

40. The method of claim 35 wherein the predetermined analyte interacts with an oxidase enzyme and the redox mediator comprises an oxidase enzyme and a peroxidase.

41. The method of claim 40 wherein the oxidase enzyme is present in an amount ranging from about 50 units to 1000 units per milliliter of the composition and the peroxidase is present in an amount ranging from 50 units to 1000 units per milliliter of the composition.

42. The method of claim 40 wherein the predetermined analyte is selected from the group consisting of glucose, alcohol, cholesterol, triglycerides and uric acid.

43. The method of claim 35 wherein the predetermined analyte exhibits peroxidase activity and the redox mediator comprises a hydroperoxide.

44. The method of claim 43 wherein the hydroperoxide is present in an amount ranging from 5 millimoles to 100 millimoles per liter of the composition.

45. The method of claim 43 wherein the predetermined analyte is selected from the group consisting of hemoglobin, a hemoglobin derivative, an erythrocyte, myoglobin and combinations thereof.

46. The method of claim 35 wherein the indicator dye is a redox indicator and is present in an amount ranging from 5 millimoles to 60 millimoles per liter of the composition.

47. The method of claim 35 wherein the metal ion complex is present in an amount ranging from 0.5 millimoles to 50 millimoles per liter of the composition.

48. The method of claim 35 wherein the cooxidant is present in an amount ranging from 5 millimoles to 100 millimoles per liter of the composition.

49. The method of claim 35 wherein the suitable carrier vehicle comprises water.

50. The method of claim 35 wherein the composition has pH in the range of from 5 to 7.

51. A method of determining the presence or concentration of occult blood in a biological fluid comprising:
   (a) contacting the biological fluid with a composition comprising an indicator dye; a hydroperoxide; a metal ion complex which includes a metal ion selected from the group consisting of a ferric ion, mercuric ion, stannic ion, nickel(II) ion, magnesium(III) ion, cadmium(II) ion, zinc(II) ion, molybdenum(V) ion, chromium(IV) ion, vanadium(III) ion, ceric(IV) ion and combinations thereof; a cooxidant selected from the group consisting of bromate ion, chlorate ion, perchlorate ion, chromate ion, a peroxide, a N-halo compound and combinations thereof; and a suitable carrier vehicle, and
   (b) determining the presence or concentration of occult blood in the biological fluid from the intensity or degree of color change of the composition.

52. A method of determining the presence or concentration of glucose in a biological fluid comprising:
   (a) contacting the biological fluid with a composition comprising an indicator dye; a hydroperoxide; a metal ion complex which includes a metal ion selected from the group consisting of ferric ion, mercuric ion, stannic ion, nickel(II) ion, magnesium(III) ion, cadmium(II) ion, zinc(II) ion, molybdenum(V) ion, chromium(IV) ion, vanadium(III) ion, ceric(IV) ion and combinations thereof; a cooxidant selected from the group consisting of bromate ion, chlorate ion, perchlorate ion, chromate ion, a peroxide, a N-halo compound and combinations thereof; and a suitable carrier vehicle, and
   (b) determining the presence or concentration of the glucose in the biological fluid from the intensity or degree of a color change of the composition.

53. A method of determining the presence or concentration of predetermined analyte in a liquid sample, said predetermined analyte interacting with an oxidase enzyme or exhibiting peroxidase activity, comprising:
   (a) contacting the liquid sample with an analyte detection device comprising a reagent test pad, the reagent test pad including a composition comprising an indicator dye; a hydroperoxide; a metal ion complex which includes a metal ion selected from the group consisting of ferric ion, mercuric ion, stannic ion, nickel(II) ion, magnesium(III) ion, cadmium(II) ion, zinc(II) ion, molybdenum(V) ion, chromium(IV) ion, vanadium(III) ion, ceric(IV) ion and combinations thereof; a cooxidant selected from the group consisting of bromate ion, chlorate ion, perchlorate ion, chromate ion, a peroxide, a N-halo compound and combinations thereof; and a suitable carrier vehicle, and
   (b) examining the analyte detection device for color transition in response to the predetermined analyte content present in the liquid sample.

54. The method of claim 53 wherein the predetermined analyte exhibits peroxidase activity.

55. The method of claim 53 wherein the predetermined analyte interacts with an oxidase enzyme.

56. The method of claim 53 wherein the predetermined analyte is selected from the group consisting of occult blood, glucose, cholesterol, alcohol, triglycerides and uric acid; and the liquid sample is a body fluid.

57. The method of claim 56 wherein the body fluid is urine, blood plasma, blood serum, gastrointestinal fluid, feces or vomit.

58. An analyte detection device to determine the presence or concentration of a predetermined analyte in a liquid test sample, said predetermined analyte interacting with an oxidase enzyme or exhibiting peroxidase activity, comprising:
   a support strip;
   a reagent test pad; and
   a composition incorporated into the reagent test pad, said composition comprising:
      (a) an indicator dye;
      (b) a redox mediator;
      (c) a metal ion complex;
      (d) a cooxidant selected from the group consisting of bromate ion, chlorate ion, perchlorate ion, chromate ion, a peroxide, an N-halo compound and combinations thereof; and
      (e) a suitable carrier vehicle.

59. The analyte detection device of claim 58 wherein the predetermined analyte exhibits peroxidase activity and the redox mediator comprises a hydroperoxide.

60. The analyte detection device of claim 58 wherein the predetermined analyte interacts with an oxidase enzyme.

* * * * *